United States Patent [19]
Haley

[11] Patent Number: 5,445,937
[45] Date of Patent: * Aug. 29, 1995

[54] DETECTION OF ALZHEIMER'S DISEASE AND OTHER DISEASES USING AN IMPROVED PHOTOAFFINITY LABELING METHOD

[75] Inventor: Boyd E. Haley, Nicholasville, Ky.

[73] Assignee: The University of Kentucky Research Foundation, Lexington, Ky.

[*] Notice: The portion of the term of this patent subsequent to Dec. 21, 2010 has been disclaimed.

[21] Appl. No.: 138,109

[22] Filed: Oct. 20, 1993

Related U.S. Application Data

[63] Continuation-in-part of Ser. No. 812,826, Dec. 24, 1991, Pat. No. 5,272,055.

[51] Int. Cl.$^6$ ............................................. C12Q 1/68
[52] U.S. Cl. ...................................... 435/6; 435/7.1; 435/7.4; 435/968; 435/188; 436/811
[58] Field of Search ................. 435/6, 4, 7.1, 7.4, 435/968, 188; 530/418, 839; 436/516, 518, 539, 546, 811; 536/23, 29

[56] References Cited
U.S. PATENT DOCUMENTS
5,272,055 12/1993 Haley ........................................ 435/6

OTHER PUBLICATIONS

Danman et al., Association–Dissociation of Mammalian Brain Glutamine Synthetase: Effect of Metal Ions and Other Ligands. Archives of Biochemistry and Biophysics 232(2):427–440, 1984.

Gunnerson et al., Detection of glutamine synthetase in the cerebrospinal fluid of Alzheimer diseased patients: A potential diagnostic biochemical marker. Proc. Natl. Acad. Sci. USA 89:11949–11953, 1992.

*Primary Examiner*—Esther M. Kepplinger
*Assistant Examiner*—Donna C. Wortman
*Attorney, Agent, or Firm*—Burns, Doane, Swecker & Mathis

[57] ABSTRACT

An improved method for diagnosing a disease comprising detecting a disease-specific biochemical marker macromolecule within a sample of extracted cerebral spinal fluid or serum is disclosed. In particular, a radioactively labeled photoaffinity probe is used to diagnose a disease. For instance, Alzheimer's disease can be diagnosed by detecting a disease-specific protein having a molecular weight of about 42,000 daltons, i.e., glutamine synthetase. Also included is a method for detecting other disease states, such as cancer, by detecting the presence or absence of specific nucleotide binding proteins.

21 Claims, 11 Drawing Sheets

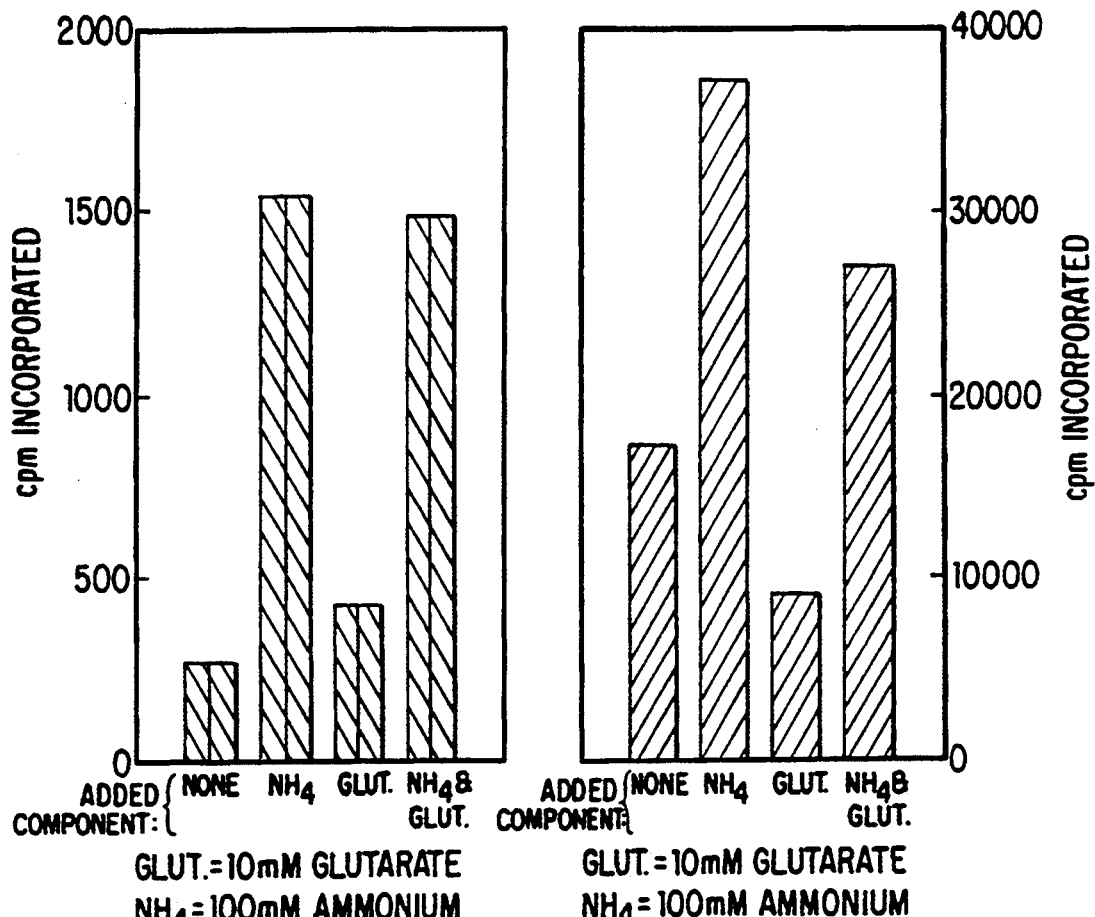

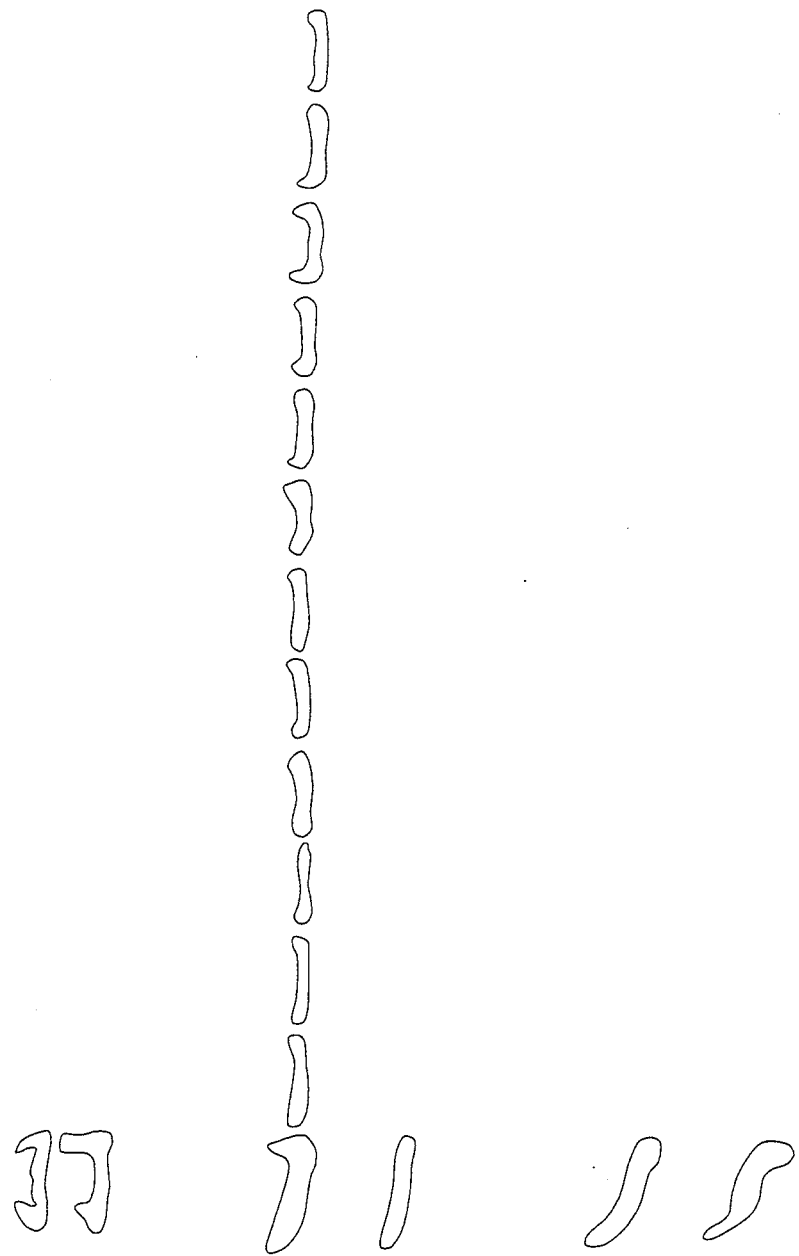

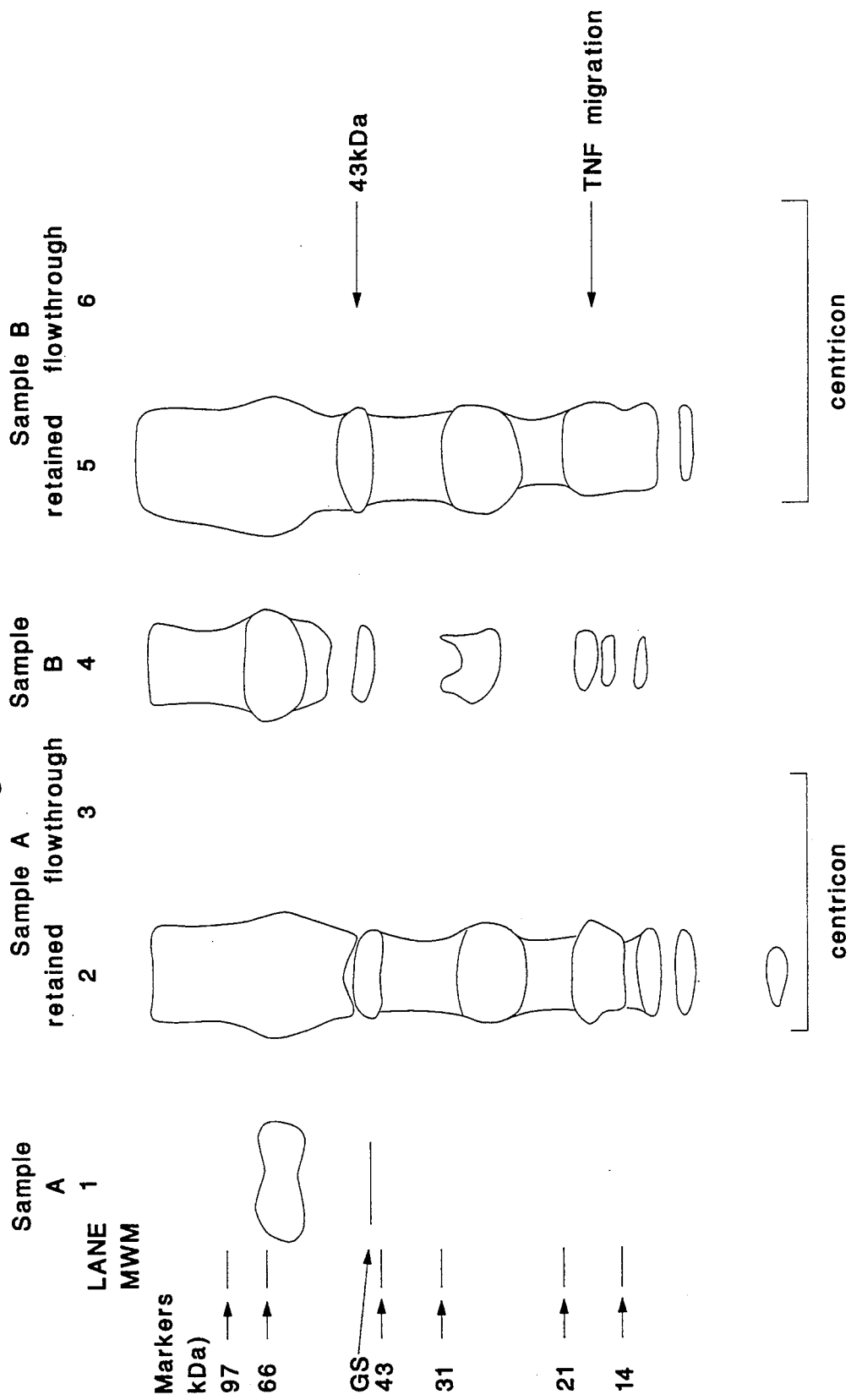

SUBJECT IDENTITY

DETECTION OF ALZHEIMER'S DISEASE AND OTHER DISEASES USING AN IMPROVED PHOTOAFFINITY LABELING METHOD

CROSS REFERENCE TO RELATED APPLICATIONS

This application is a continuation-in-part of U.S. Ser. No. 07/812,826, filed Dec. 24, 1991 U.S. Pat. No. 5,272,055.

FIELD OF THE INVENTION

The present invention relates to novel compositions, methods and test kits which use the procedure of photoaffinity labeling with nucleotide affinity probes, to detect disease using cerebral spinal fluid, blood, tissue, or other specimens in a mammal. The present invention provides a method of diagnosis based on a disease-specific biochemical marker macromolecule which, if present, can be identified in a small biological sample from a patient. In particular, the present invention concerns a method for diagnosing particular disease states using a disease-specific nucleotide binding protein and detecting the binding of that protein in the serum or cerebral spinal fluid of a patient afflicted with that disease.

BACKGROUND OF THE INVENTION

Alzheimer's disease (AD) is an idiopathic progressive dementia that will affect a large percentage of our aging population. To date its etiology is still unknown. The neurodegenerative disease is characterized by a chronically deteriorating course of impaired intellectual function and memory loss.

Relatively little is known of the pathophysiological chain of events that leads to the premature dysfunction and death of affected neurons in Alzheimer's disease patients. Multiple abnormalities have been reported in the brains of patients who have been diagnosed as having Alzheimer's disease, but it is difficult to determine which of these are the result of brain damage and which contribute to premature neuronal dysfunction and death.

At the present time, the clinical diagnosis of Alzheimer's disease is one of exclusion. Secondary causes of loss of memory and impaired cognitive function may result from multiple infarcts, leading to so-called multi-infarct dementia, or from intracranial mass lesions, such as subdural hematomas, brain tumors, or granulomas. Central nervous system infections of viral and bacterial origin, or even slow viral disorders such as Creutzfeldt-Jakob disease, are part of the differential diagnosis. Furthermore, metabolic disorders involving vitamin $B_{12}$ metabolism, thiamine or folate deficiency, thyroid dysfunction, hepatic and renal failure, as well as drug toxicity may appear as dementia. Nevertheless, when all these secondary causes, many of which are reversible, are eliminated, cerebral atrophy of unknown cause or Alzheimer's disease still covers the largest number of patients.

The definitive diagnosis of Alzheimer's disease is made by pathologic examination of postmortem brain tissue in conjunction with a clinical history of dementia. This diagnosis is based on the presence in brain tissue of intraneuronal neurofibrillary tangles and of neuritic (senile) plaques, which have been correlated with clinical dementia. Although the cause of the abnormal cytoskeletal fibrils remains unknown, neuritic plaques are thought to be composed of degenerating axons and nerve terminals as well as possible astrocytic elements, and they often exhibit a central amyloid protein core. The neurofibrillary tangles are interneuronal aggregates composed of normal and paired helical filaments and presumably consist of several different proteins. The neurohistopathologic identification and counting of neuritic plaques and neurofibrillary tangles requires staining and microscopic examination of several brain sections.

It is problematic, however, that histochemical staining is not always reproducible, neuritic plaques and neurofibrillary tangles are not uniformly distributed, and histopathologic studies are time-consuming and labor-intensive. Moreover, there is no direct evidence that an accumulation of abnormal cytoskeletal fibrils contributes directly to premature dysfunction and death of the neurons; rather, the fibrils may simply be a manifestation of more fundamental cellular changes. The clinical and pathologic progression of Alzheimer's disease is marked by a continuing loss of neurons from the cerebral cortex. However, neuritic plaques and neurofibrillary tangles may occur in nondemented elderly patients, as well as those afflicted with Alzheimer's disease.

Current research to develop both an understanding of the disease and a possible diagnostic test has centered on the amyloid protein and its precursor protein. Theoretically, diagnosis has been based on the deposition of amyloid containing plaques in the cortical region in the brain of individuals affected with Alzheimer's disease. Such diagnostic methods have been disclosed in, for example, U.S. Pat. Nos. 4,666,829, 4,701,407, 4,816,416 and 4,933,156.

However, amyloid deposits are also found in the brains of aged individuals who have never displayed signs of dementia. For example, a recent article (*J. Biol. Chem.*, 265:15977 (1990)) has shown that there were no differences in the primary structure of precursor amyloid protein from platelets of normal individuals and that of Alzheimer's disease patients. Therefore, while amyloid protein may be involved in Alzheimer's disease, other methods have been pursued to identify characteristics more uniquely related to a patient with Alzheimer's disease. For instance, U.S. Pat. No. 4,727,041, issued to Aroonsakul, discloses a comparative test for the diagnosis of Alzheimer's disease in humans by determining levels of somatotropin and somatomedin-C in the patient's blood sera drawn at intervals following administration of an L-dopa provocative test.

Immunoassay methods have also been developed for detecting the presence of neurochemical markers in Alzheimer's disease patients. U.S. Pat. Nos. 4,728,605 and 4,801,533, issued to Fudenberg et al., disclose comparative methods for diagnosing degenerative disease of the central nervous system, particularly Alzheimer's disease, by measuring immunological parameters and interactive T cells from a patient's peripheral blood. U.S. Pat. No. 4,806,627, issued to Wisniewski et at., discloses protease resistant proteins which comprise scrapie-associated fibrils and a scrapie-specific monoclonal antibody to distinguish certain neurological disease-caused human dementias from Alzheimer's disease.

However, none of the known methods of diagnosis have proven to be a reliable means of detection of Alzheimer's disease in all patients, particularly at early stages of the disease. As a result, alternative methods of diagnosis have been proposed which rely on analyzing the cerebral spinal fluid drawn from the affected patients. For example, Warner in *Anal. Chem.*, 59:1203A-1204A (1987), has proposed a method for detecting Alzheimer's disease related amyloid protein in the cerebral spinal fluid of affected patients.

U.S. Pat. No. 4,874,694, issued to Gandy et al., discloses a diagnostic method for neurological and psychiatric disorders, such as Alzheimer's disease. The method involves incubating cerebrospinal fluid from a patient in the presence of $^{32}$P-labeled adenosine triphosphate (ATP) and a protein kinase which was capable of transferring phosphate from the ATP, followed by electrophoresis. The resulting autoradiographic pattern of the fractionated, labeled sample is then compared with predetermined autoradiographic patterns from known neurological and psychiatric pathologies to ascertain the particular pathology of the patient's cerebrospinal fluid being analyzed. However, the method disadvantageously is based only on autoradiographic patterns. It fails to identify disease-specific marker proteins in the cerebral spinal fluid.

Studies by Khatoon et at. (*Ann. of Neurology*, 26:210–215 (1989)) have shown that an interaction of an important cellular protein, tubulin, in the formation of microtubules was aberrant in preparations made from the brain tissues of patients with Alzheimer's disease. The inhibition was monitored by measuring the interactions of a radioactive photoaffinity probe of the nucleotide GTP (guanosine-5'-tri-phosphate) with the proteins that require GTP to effect microtubule formation.

Molecules containing azido groups have been shown to form covalent bonds to proteins through reactive nitrene intermediates, generated by low intensity ultraviolet light. Potter & Haley, *Meth. in Enzymol.*, 91:613–633 (1983). In particular, 2- and 8-azido analogues of purine nucleotides have been used as site directed photoprobes to identify nucleotide binding proteins in crude cell extracts. Owens & Haley, *J. Biol. Chem.* 259:14843–14848 (1984); Atherton et al., *Bio. of Reproduction*, 32:155–171 (1985). The 2-and 8-azido nucleotides have also been used to map nucleotide binding domains of purified proteins. Khatoon et al., *Ann. of Neurology*, 26:210–215 (1989); King et al., *J. Biol. Chem.*, 264:10210–10218 (1989); and Dholakia et al., *J. Biol. Chem.*, 264:20638–20642 (1989).

Photoaffinity probes have been used to determine specific nucleotide binding sites on a biologically active recombinant peptide molecule. Campbell et al., *PNAS*, 87:1243–1246 (1990). The probes have also been used to study enzyme kinetics of purified proteins. Kim et al., *J. Biol. Chem.*, 265:3636–3641 (1990).

Thus, considerable effort has been devoted to developing systems for the definitive diagnosis of Alzheimer's disease in patients. However, until the method of the present invention, no reliable non-invasive test for Alzheimer's disease has been developed. The major drawback of the most definitive determination of Alzheimer's disease known in the art has been that direct analysis of pathological tissue could only be performed postmortem on affected individuals.

Because Alzheimer's disease is progressive in nature, the efficiency of a cure could critically depend upon early detection. Additionally, the value of any new therapy in alleviating or curing the disease could be better ascertained if a rapid, safe and effective diagnostic procedure were available to monitor the progress of Alzheimer's disease patients following treatment. The same can be said for other disease states, such as cancer.

Therefore, there remains a long-felt need in the art for a reliable, accurate, safe and effective method for the diagnosis of Alzheimer's disease, as well as a means for the diagnosis and differentiation of other diseases, syndromes or pathologies. A method for the identification and characterization of a disease-specific biochemical marker and the identification of such a marker is needed.

OBJECTS AND SUMMARY OF THE INVENTION

It is, therefore, an object of this invention to provide a method for diagnosing Alzheimer's disease comprising detecting a specific nucleotide binding protein within the extracted cerebral spinal fluid of patients afflicted with Alzheimer's disease.

It is another object of the present invention to provide a method for diagnosing Alzheimer's disease comprising detecting a specific nucleotide binding protein within the extracted cerebral spinal fluid of normal patients, but which is not photolabeled in the cerebral spinal fluid of patients afflicted with Alzheimer's disease.

It is a further object of the present invention to provide a composition for use in a test kit for the diagnosis of Alzheimer's disease comprising a radioactive photoaffinity probe which will selectively bind to a specific nucleotide binding protein within the extracted cerebral spinal fluid of a patient afflicted with Alzheimer's disease, but which is not found in the cerebral spinal fluid of a normal subject.

A still further object of the present invention is to provide a composition for use in a test kit for the diagnosis of Alzheimer's disease comprising a radioactive photoaffinity probe which will selectively bind to a specific nucleotide binding protein within in the cerebral spinal fluid of a normal patient, but which is not found in the cerebral spinal fluid of a patient afflicted with Alzheimer's disease.

It is an additional object of the present invention to provide antibodies to the respective Alzheimer's disease related proteins, as identified by the method of the current invention, for the purpose of providing an immunoassay to recognize the Alzheimer's disease specific proteins in the cerebral spinal fluid, blood plasma, or tissues of the human body.

It is another object of the present invention to provide a method, using the procedure of photoaffinity labeling with nucleotide affinity probes, to diagnose neurological disorders using cerebral spinal fluid, blood, tissue, or other biological samples from a mammal. The presence or development of a neurological or psychiatric pathology including, but not limited to, Alzheimer's disease, epilepsy, scrapies-type disorders, amyotrophic lateral sclerosis (ALS or Lou Gehrig's disease), Down's syndrome, Behcet disease, encephalitis, Huntington disease, Creutzfeldt-Jakob disease, Parkinson disease, AIDS dementia, multiinfarct dementia, dystonia, ataxia, schizophrenia, neurosyphilis, cerebral toxoplasmosis, brain irradiation, brain tumor, Guillain-Barre syndrome, tremor, multiple sclerosis, head trauma, acute and chronic encephalitic and vascular disease, or other disease states such as cancer or eating disorders such as anorexia can be detected.

A still further object of the present invention is to provide a method for aiding in the diagnosis of a specific neurological disease wherein the neurological disease demonstrates elevated glutamine synthetase in the cerebral spinal fluid as detected by photoaffinity labeling with a radioactive nucleotide photoaffinity probe, and wherein the photoincorporation of that probe is considerably elevated by the addition of micromolar levels of $Mn^{2+}$ metal ion.

Yet a further object of the present invention is to provide a method for aiding in the diagnosis of a specific neurological disease wherein the neurological disease shows an elevation of one or more proteins readily observable after dialysis or filtration of the small molecules away from the proteins of CSF.

A still further object of the present invention is to provide a method for aiding in the diagnosis of other disease states, including non-neural disease states, such as cancer, wherein a sample obtained from a patient suffering from that disease shows an elevation or a decrease in one or more proteins that are detectable by photoaffinity labelling.

Additional objects, advantages and novel features of the invention will be set forth in part in the description which follows, and in part will become apparent to those skilled in the art on examination of the following description, or may be learned by practice of the invention.

BRIEF DESCRIPTION OF THE DRAWINGS

FIG. 3 shows two bar graphs which compares the photolabeling with $[^{32}P]2N_3ATP$ of the 42,000 $M_r$ protein of cerebral spinal fluid (3A) from Alzheimer's diseased patients with that of purified glutamine synthetase (GS) (FIG. 3B). Photolabeling was done under different conditions (e.g., with or without added $NH_4+$) and the proteins were separated by SDS-PAGE. The 42,000 $M_r$ band was excised and the level of $^{32}P$ incorporated was determined. Such experiments were used to show that the 42,000 $M_r$ protein and GS behaved identically under several different biochemical conditions and, Western blotting with the GS specific antibody data, confirmed that the 42,000 $M_r$ protein was indeed GS.

FIG. 5A is an SDS-PAGE gel showing pure GS.

FIG. 6B is an autoradiogram of the gel from FIG. 6A showing the enhancement of photolabeling of GS and four other proteins in these samples by Centricon filtration.

DETAILED DESCRIPTION OF THE PREFERRED EMBODIMENTS OF THE INVENTION

Figure 1:
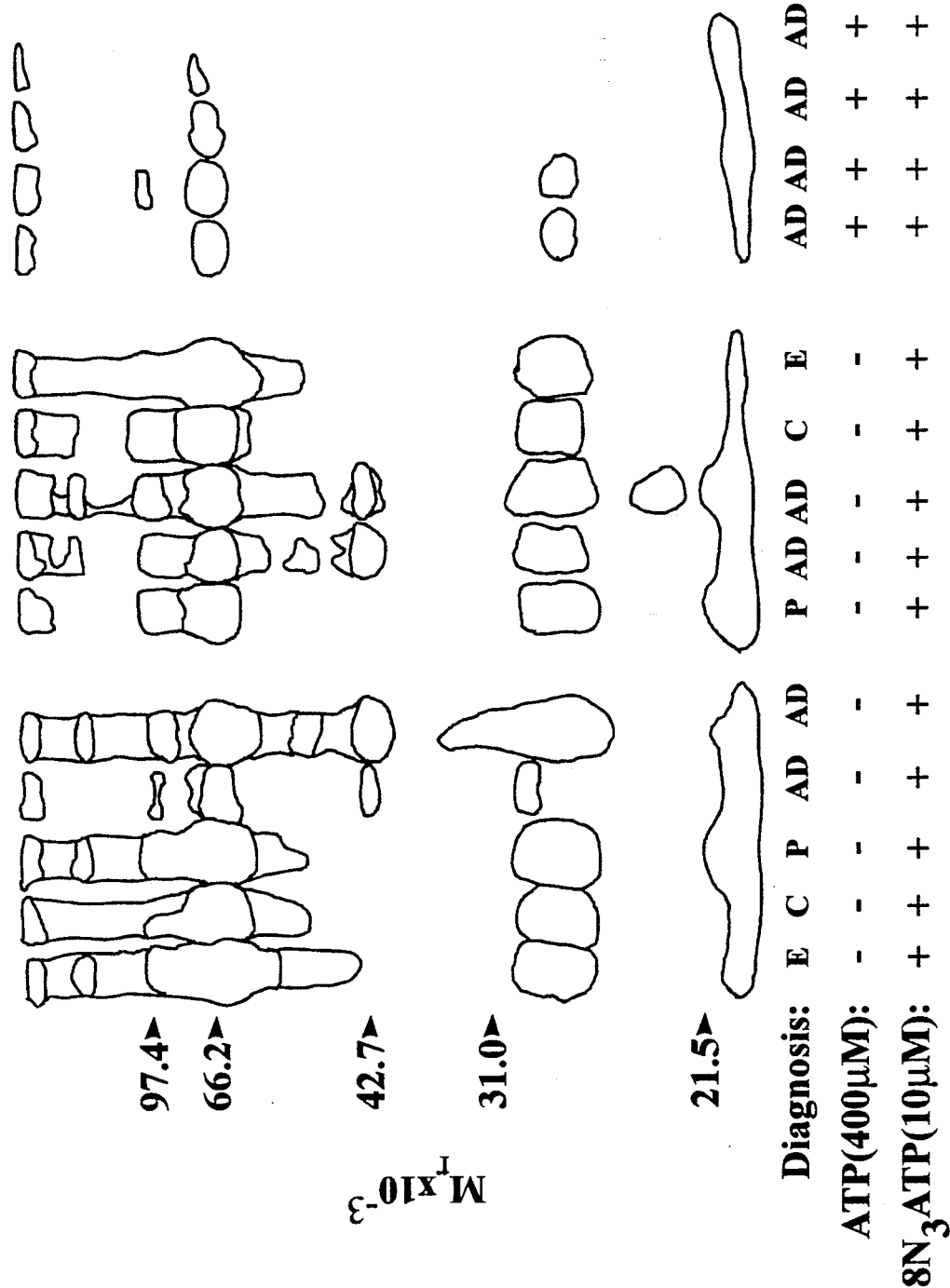
FIG. 1 is a photograph of an autoradiogram made from a sodium dodecyl sulfate-polyacrylamide gel (SDS-PAGE) on which human cerebral spinal fluid proteins were separated after being photolabeled with $[^{32}P]8N_3ATP$. The cerebral spinal fluid samples were obtained from patients known to have epilepsy (lanes E), Parkinson's disease (lanes P), Alzheimer's disease (lanes AD) or from normal, age-matched control subjects (lanes N). The autoradiograph shows that a protein of about 42,000 $M_r$ is photolabeled only in the cerebral spinal fluid of a patient with Alzheimer's disease. Also, the selectivity of this interaction with naturally occurring ATP is demonstrated by the prevention of photolabeling by $[^{32}P]8N_3ATP$ when ATP is present as shown in the last four lanes.
Figure 2A:
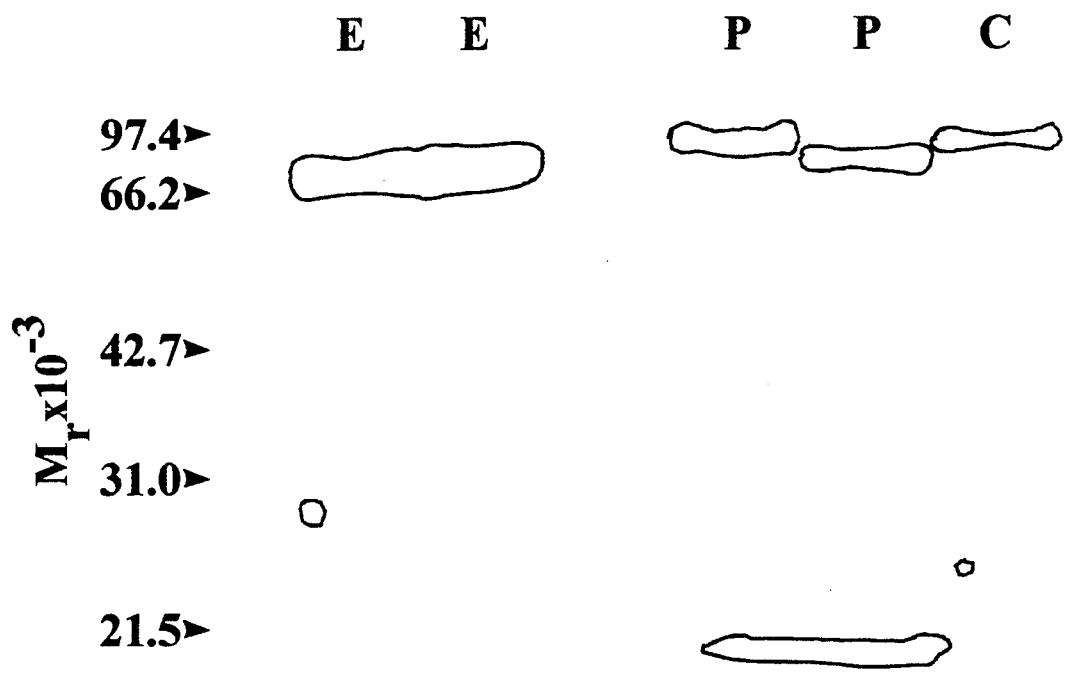
FIGS. 2A and 2B is a photograph of two combined autoradiographs of the two 10% SDS-PAGE shown in FIGS. 2 C and D on which human cerebral spinal fluid proteins were separated after photolabeling with $[^{32}P]8N_3cAMP$. These are the same patient samples used in FIG. 1. Samples were from patients with epilepsy (lanes E), Parkinson's disease (lanes P), Alzheimer's disease (lanes AD), or from normal control subjects (lanes N). The lane labeled "markers" contained proteins of known molecular weight which were used to determine the approximate molecular weight ($M_r$ value) of the cerebral spinal fluid proteins. The SDS-PAGEs were stained with Coomassie Brilliant Blue R (CBB) to detect cerebral spinal fluid proteins of different $M_r$ values and are shown in FIGS. 2 C and D. Proteins photolabeled with $[^{32}P]8N_3cAMP$, since they are now radioactively tagged, were located by autoradiography as shown in FIGS. 2A and 2B. The data in the autoradiographs of FIGS. 2A and 2B show that a protein of about 68,000 $M_r$ is photolabeled only in the cerebral spinal fluid of normals, epileptics and Parkinson's diseased individuals. This 68,000 $M_r$ protein is not photolabeled in the cerebral spinal fluid of Alzheimer's diseased patients.
Figure 2B:
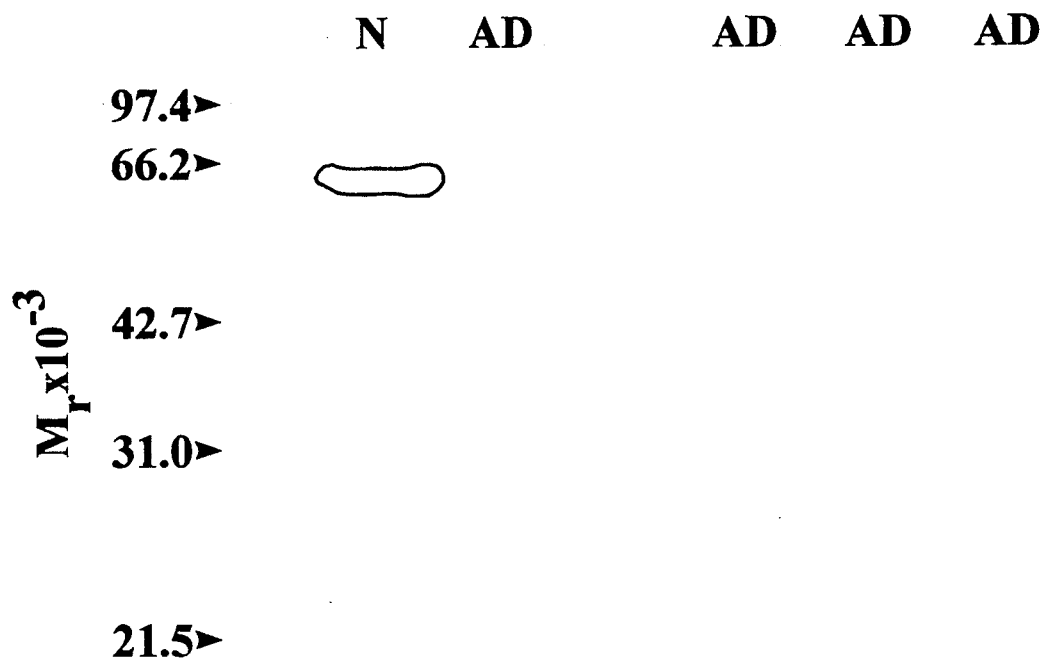
Figure 2C:
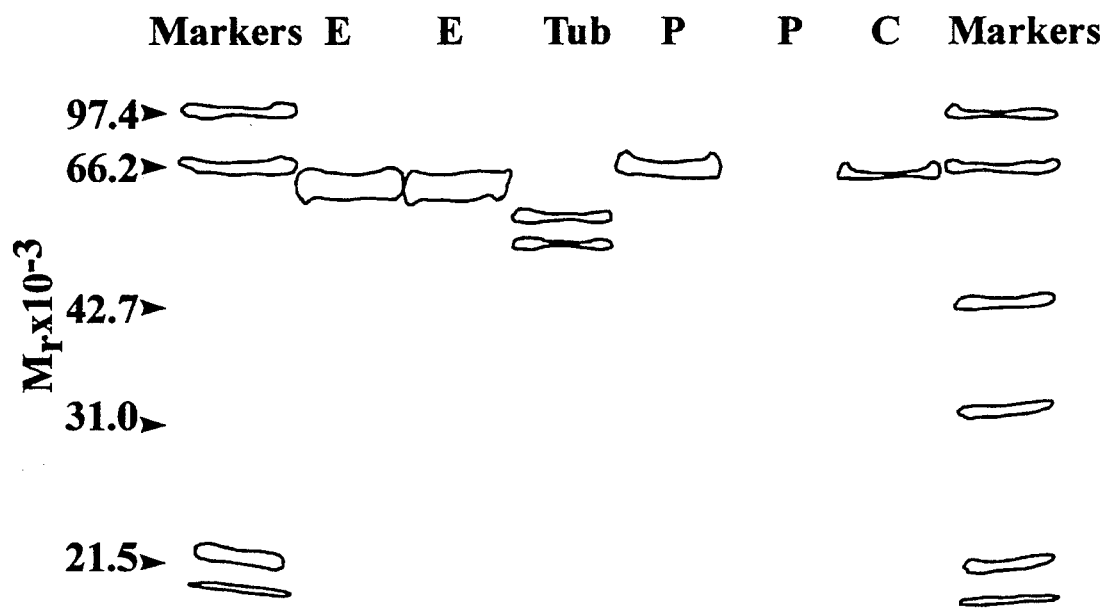
Figure 2D:
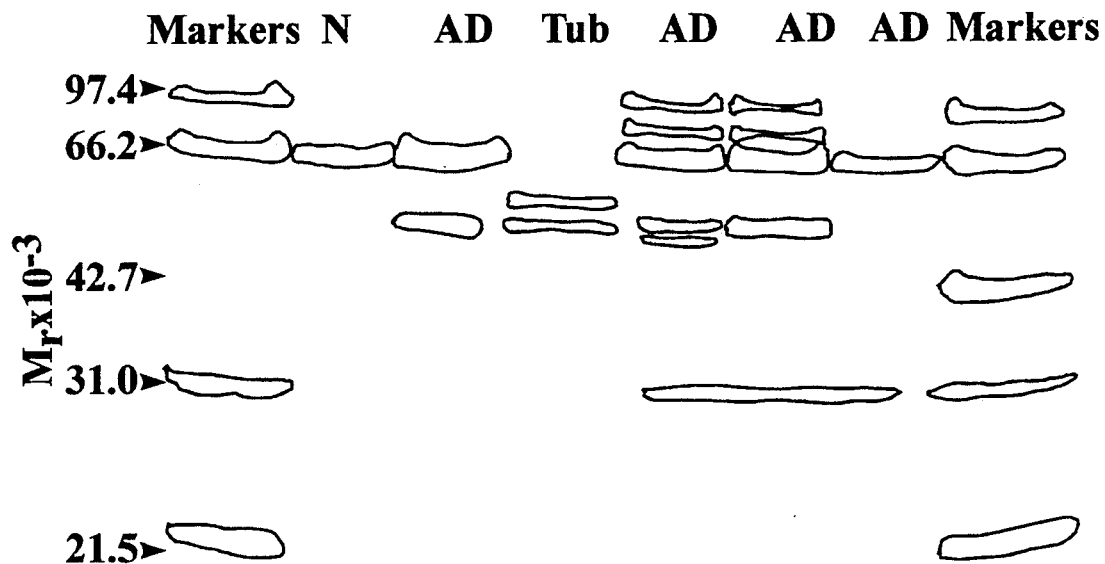

In accordance with the present invention, novel compositions, methods and test kits are provided, using the procedure of photoaffinity labeling with nucleotide affinity probes, to detect a neurological disorder using cerebral spinal fluid, blood, tissue, or other biological samples from a mammal. The presence or development of a neurological or psychiatric disorder can be detected. The invention concerns a composition, the preparation of the composition and a method for diagnosing or detecting Alzheimer's disease. The method involves the use of a disease-specific nucleotide binding protein within the extracted cerebral spinal fluid of a patient afflicted with a neurological disorder such as Alzheimer's disease.

The present invention provides a method for detection using a disease-specific biochemical marker macromolecule which, if present, can be identified in a small biological sample obtained from a patient. The specific biochemical marker macromolecule is dependent on the disease state which is being detected.

The standards for testing for neurological disease states are established by obtaining cerebral spinal fluid samples from a number of patients, each of whom suffers from a particular disorder which is clinically manifested by marked dementia or deficiency in cognitive function, including memory or attention.

Specifically the neurological diseases of the nervous system, referred to in the method of the present invention are those diseases, disorders, or syndromes which are either the cause of or the result of a biochemical alteration in the brain, brain stem, spinal cord or ganglia. The diseases can include, but are not limited to, Alzheimer's disease, epilepsy, scrapies-type disorders, amyotrophic lateral sclerosis (ALS or Lou Gehrig's disease), Down's syndrome, Behcet disease, encephalitis, Huntington disease, Creutzfeldt-Jakob disease, Parkinson disease, AIDS dementia, multiinfarct dementia, dystonia, ataxia, schizophrenia, neurosyphilis, cerebral toxoplasmosis, brain irradiation, brain tumor, Guillain-Barre syndrome, tremor, multiple sclerosis, head trauma, acute and chronic encephalitic and vascular disease. Moreover, the present method of detection could also be used to monitor any event which causes brain cell death which results in the accumulation of nucleotide binding proteins in the cerebral spinal fluids, such as, minor to severe brain damage caused by high fever or head injury. The present invention can also be utilized to detect other disease states such as cancer, which also lead to alterations in the level of biochemical marker macromolecules.

By the present invention it has been shown that a disease-specific unique biochemical marker macromolecule, in particular a specific nucleotide binding protein, can be identified in the spinal fluid of patients suffering from certain neurological disorders, particularly patients suffering from Alzheimer's disease. Additionally, it has also been shown that proteins obtained from fluid samples from cancer patients show altered photolabeling compared to normal patients.

Briefly, a typical analysis of a cerebral spinal fluid sample or serum by the method of the present invention would proceed as follows. These steps and quantities are only offered as guidelines for the practice of the present invention.

A small portion, usually between 10 to 30 microliters of cerebral spinal fluid or serum is mixed with concentrations of about 10 to 30 $\mu$M of a radioactive radioaffinity probe for 0.5 to 1.0 minutes, followed by 30 to 120 seconds of exposure to ultraviolet light. Photoincorporation of [$^{32}$P]8N$_3$ATP into GS is preferably elevated by the addition of micromolar levels of Mn$^{2+}$ metal ion. Suitable levels of Mn$^{2+}$ metal ion range from 1.0 $\mu$M to 1000 $\mu$M, more preferably 5 $\mu$M to 50 $\mu$M, and most preferably 10 $\mu$M. The sample is precipitated, then immediately solubilized with a solution containing detergent and subjected to protein fractionation, such as by gel electrophoresis. In a preferred embodiment, prior to photolabeling, CSF or serum samples are filtered by dialysis or filtration using a filtration device such as a Centricon filter. Such filtration or dialysis removes small molecules from the CSF or serum which interfere with photolabeling.

The finished gel is placed in a holder containing X-ray film for autoradiography. The radioactive protein (the result of chemical crosslinking between the radioactive photoprobe and the binding protein) in the gel can be located since the radioactivity will expose the adjacent section of the film resulting in a darkened (black) appearance.

The sample subjected to analysis can be selected from any biological sample capable of carrying the unique nucleotide binding protein. Examples of such biological samples include body fluids such as spinal fluid, blood or serum. However, samples tested for the unique nucleotide binding protein by the present method are most preferably cerebral spinal fluid, also referred to as cerebrospinal fluid or serum.

The protein composition of cerebral spinal fluid is largely derived from serum proteins which leak into the subarachnoid space through imperfections in the blood brain barrier, such as the area postrema, and perhaps across the richly vascular choroid plexus, through which cerebral spinal fluid is generated as an ultrafiltrate. The cerebral spinal fluid has significantly fewer proteins than cytosolic fractions. Some proteins, such as immunoglobulins, may be generated in the subarachnoid space during inflammation. Since the cerebral spinal fluid bathes the surfaces of cerebral and cerebellar cortices, the caudate, brain stem and spinal cord, each of the structures contributes to the total cerebral spinal fluid protein.

The inventive method need not be limited to human patients, but may be extended to any mammal afflicted with certain diseases or syndromes, including scrapies or "Mad Cow" disease.

The sample may be drawn as either ventricular cerebral spinal fluid or as lumbar cerebral spinal fluid, or as a blood sample. Occasionally, however, sample proteins are concentrated by various procedures to better visualize the specific nucleotide binding protein. Vacuum procedures include, for example, lyophilization or Speed-vac concentration. Also, precipitation of cerebral spinal fluid by ammonium sulfate or polyethylene glycol could be used to concentrate the nucleotide binding proteins. Thus, there are a variety of techniques well known in the art that would be suitable in the practice of the present invention.

Detection of a specific nucleotide binding protein can be accomplished by measuring a label crosslinked to the selected biochemical marker macromolecule after reaction, photochemical or chemical crosslinking, and removal of free probe. The particular label bound to the macromolecule will include, for example, a radioactive nucleotide introduced by replacing an equivalent non-radioactive atom with $^{32}$P, tritium, carbon-14 or other radioactive atom or ligand analog modified with a linker group to provide a linking site to the crosslinking molecule. A particularly preferred radioactive label in the present invention is $\alpha$- or $\gamma$-$^{32}$P.

The ligand or linker group, if present on the specific biochemical marker macromolecule, will have chemical characteristics or functionalities such that a small radioactive nuclide labeled molecule, or a chromogenic, fluorogenic, or luminescent molecule, or a magnetic particle can be attached to the ligand or linker group. The ligand will have the chemical characteristics such that a receptor molecule is available or capable of being elicited, such as an antibody molecule to the ligand. The receptor molecule can be conjugated to a radioactive nuclide labeled molecule, or to a chromogenic, fluorogenic, or luminescent dye molecule, or to a magnetic particle or to an enzyme system capable of generating a chromogenic, fluorogenic, and/or luminescent product via appropriate substrates.

Most preferably the unique biochemical marker macromolecule, particularly the specific nucleotide binding protein, is detected in the sample by a radioactively labeled photoaffinity probe. A nucleotide photoaffinity probe is a nucleotide derivative which has affinities for binding sites and biological activity comparable to the unaltered nucleotide. Exposure to certain wavelengths of light converts the analog to a very reactive intermediate, typically a nitrene or a carbene, which may result in covalent incorporation into the binding site if it is bound to a protein.

There are certain advantages to using photoprobes over conventional chemical probes. One advantage is that $K_m$, $K_d$, and $K_i$ values can be determined in the absence of activating light. Another advantage is that complex systems such as ribosomes, membranes, and whole cell sonicates can be studied. In this manner, an in vivo situation may be more closely approximated and information may be obtained that might otherwise be lost in a purified system.

Many nucleotide photoaffinity probes may be synthesized and used successfully. The photoaffinity compounds of the invention may include, for example, purine triphosphate azido analogs, which may be exemplified by adenine analogs, although guanine analogs can be substituted therefor. For example, purine binding sites may be effectively labeled by the following, and their 5'-mono-, di- and triphosphates: oligomers of a single azidoadenylyl species, such as, for example: 2-azido or 2-azidoadenylyl(2'-5')2-azidoadenylyl(2'-5')2-azidoadenosine; 2-azido or 8-azidoadadenosine; 8-azidoadenylyl(2'-5')-8-azidoadenylyl(2'-5')8-azidoadenosine; 8-azidoadenylyl(2'-5')-8-azidoadenylyl(2'-5')8-azidoadenylyl-(2'-5')8-azidoadenosine; 2,8-diazidoadenylyl(2'-5')2,8-diazidoadenylyl(2'-5')2,8-diazido-adenosine; 2,8-diazidoadenylyl(2'-5')2,8-diazidoadenylyl(2'-5')2,8-diazidoadenylyl(2'-5')2,8-diazidoadenosine; also oligomers of AMP and a single azidoadenylyl species, such as, for example: 2-azidoadenylyl(2'-5')2-(2'-5')adenosine; adenylyl(2'-5')8-azidoadenylyl(2'-5')8-azidoadenosine; also oligomers containing more than one azidoadenylyl species, such as, for example: 2-azidoadenylyl(2'-5')8-azidoadenylyl(2'-5')2-azidoadenosine; also oligomers resulting from any combination of the monomers AMP, 2-azido-AMP, 8-azido-AMP and/or 2,8-diazido-AMP, provided that at least one such monomer incorporated into the oligomer is an azido-AMP species.

In addition photoaffinity compounds of the invention may also include photoactive coenzyme analogs of $NAD^+$, exemplified by nicotinamide 2-azidoadenosine dinucleotide (2-azido-$NAD^+$), or analogs of NADH, exemplified by nicotinamide 2-hydrazidoadenosine dinucleotide (2-azido-NADH).

Alternatively, guanine moieties can be defined in each of the exemplary compounds in place of the respective adenine moieties. Therefore, certain most preferred compounds of the present invention are synthesized from azidoguanosine 5'-triphosphates or combinations thereof, or from azidoguanosine 5'-triphosphates and ATP. The latter provides a (2'-5')oligomer containing both guanylyl and azidoguanylyl moieties.

Furthermore, photoaffinity compounds of the present invention may also include, for example, pyrimidine derivatives. For instance, photoactive analogs of dUTP, such as 5-azido-2'-deoxyuridine 5'-triphosphate (5-$N_3$dUTP), may be synthesized from dUMP and provide a pathway for the synthesis of other useful 5-substituted uridine nucleotides. The 5-diazouridine nucleotides may, for example, serve as active-site-directed photoaffinity probes or as substrates for polymerizing enzymes to generate additional photoactive nucleic acids which remain stable to extremes of pH and which remain effective photolabeling reagents in the presence of reducing agents. Moreover, since the synthesis of 5-$N_3$dUTP employs mild conditions, it is also possible to synthesize homopolymers of 5-$N_3$dUTP to provide single-stranded photoactive DNA of defined length. Using 5$N_3$UTP one can similarly produce photoactive RNA.

Generalized methods for the synthesis of aryl azides include nucleophilic displacement of a bromine, chlorine or nitro group by an azide ion or the addition of sodium azide to an acidic solution containing a diazotized primary aromatic amine.

To date the most widely used 8-azidopurine is probably 8$N_3$cAMP. One of the advantages of 8$N_3$cAMP is that in mammalian systems there are only two types of proteins that are known to bind cAMP with high affinity, the cAMP phosphodiesterases and the regulatory subunits of the cAMP-dependent protein kinases. The photoprobes [$^{32}$P]8$N_3$cAMP and [$^{32}$P]8$N_3$ATP have been employed to study, for example, the mechanisms of action of cAMP-dependent protein kinase. Photoactive analogs of GTP, e.g., [$^{32}$P]8$N_3$GTP, have been developed to study, for example, tubulin polymerization, while photoactive analogs of UTP, e.g., [$^{32}$P]5$N_3$dUTP have been generated to study, for example, the binding site of DNA binding proteins.

Preferred compounds of the present invention are synthesized from azidoadenosine 5'-triphosphates or combinations thereof, which provide a (2'-5')oligomer containing both adenylyl and azidoadenylyl moieties. A preferred photoaffinity compound for the identification by the present invention of the Alzheimer's disease-specific protein is 8-azidoadenosine 5'-triphosphate (8$N_3$ATP), while a particularly preferred photoaffinity compound of the present invention is 2-azidoadenosine 5'-triphosphate (2$N_3$ATP). A particularly preferred photoaffinity compound for the identification by the present invention of the ALS-specific protein is 8-azidoguanosine 5'-triphosphate (8$N_3$GTP). Particularly preferred photoaffinity compounds for the identification by the present invention of the cancer-specific proteins are 8-azidoadenosine 5'-triphosphate (8$N_3$ATP) and 2-azidoadenosine 5'-triphosphate (2$N_3$ATP).

Nonradioactive labels can be divided into two categories (i) chromogenic, fluorogenic, or chemiluminescent dyes or (ii) ligands. Dyes are normally of from 8 to 40 carbon atoms, preferably from 9 to 30 carbon atoms. The dyes further normally contain from 1 to 10 heteroatoms usually oxygen, nitrogen, or sulfur, and normally contain no halogen atoms or up to 10 halogen atoms usually iodine, bromine, chlorine, or fluorine.

Chromogenic dyes may include phenol sulfonephthalein and analogs of tetrazolium.

Fluorogenic dyes may include fluorescein isothiocyanate, dichlorotriazinylamino fluorescein, morpholinorhodamine isothiocyanate, tetramethylrhodamine isothiocyanate, and 4-acetamido-4-isothiocyano-stilbene-2 with 2'-disulfonic acid. Fluorescent purine derivatives may also include, for example, the fluorescent GTP analog 2'3'-O-(2,4,6-trinitrocyclohexadienyl-idine)-guanosine 5'-triphosphate (TNP-GTP), or the equivalent fluorescent ATP derivative (TNP-ATP).

Chemiluminescent dyes may include 5-amino-2,3-dihydro-phthalazine-1,4-dione (luminol), derivatives of isoluminol and acridinium esters.

Any ligand may be employed for which an appropriate receptor may be found to have satisfactory specificity for the ligand.

Various methods or protocols may be employed in measuring the amount of the labels. These protocols can include for example, radioimmunoassay (RIA), immunoradiometric assay (IRMA), sandwich IRMA, fluoroimmunoassay (FIA), chemiluminescent assays, bioluminescent assays, and enzyme linked immunosorbent assays (ELISA) among others.

The labeled probe of the present invention can be used in any conventional hybridization technique. Hybridization formats which may be useful in the practice of the present invention include those in which the sample is immobilized on a solid support (solid-phase hybridization) and those wherein the species are all in solution (solution hybridization). Solution hybridization is preferred in the present method. Another method of interest is the sandwich hybridization technique.

Certain factors are considered when a unique biochemical macromolecular marker is identified by means of a radioactive photoaffinity label, as is the preferred method of the present invention. For example, consideration should be given to: (a) temperature of incubation and photolysis, (b) length of incubation and photolysis, (c) concentration of photoaffinity reagent, (d) binding affinity of protein for the reagent and natural ligands, (e) stability of the photoaffinity reagent in each particular system, (f) ionic strength, pH, cofactors, (g) protein concentration, (h) intensity of photolyzing light, (i) quenching of reaction and separation of unused label, and (j) interpretation of results. Potter & Haley in *Meth. in Enzymol.*, 91:613-633 (1983) provide a detailed account of preferred procedures for labeling a specific biochemical marker macromolecule in a sample with a photosensitive purine triphosphate azide analog.

Temperature of the photolysis reaction between the sample and the selected photoaffinity label can range from 0° C. to room temperature (25° C.) or above. However, the exchange rate between bound and unbound cAMP or 8-$N_3$cAMP approaches negligible levels at 0° C., and is greatly increased at room temperature. Conversely, once 8-$N_3$cAMP is bound to the specific macromolecular marker, it may be cold trapped onto the protein by dropping the temperature to nearly 0° C. Therefore, the most preferred procedure includes preincubation of the components at room temperature, and photolysis in plates set on ice to reduce the temperature to approximately 0° to 4° C. By the present invention, the sample is preferably incubated at room temperature with the radioactive photoaffinity probe for approximately 0.5 to 1.0 minutes. Most preferably the mixture is vortexed for 6 seconds followed by an additional 24 seconds of mixing, immediately followed by placing the sample on ice for photoactivation.

The concentration of photoaffinity reagent must be compatible with the binding affinity of the protein to be labeled. Excessively high concentrations, however, can lead to undesirable nonspecific labeling which increases linearly with concentration. Best results can be obtained by experimentally determining the optimum concentration for photoincorporation. Directly related to the determination of concentration is the stability of the reagent. The stability of the reagent can be determined by thin-layer chromatography, e.g., by fluorescent cellulose thin-layer chromatography.

Ionic strength, pH, cofactor, and metal ion concentrations can each affect protein structure, and are readily adjusted by those skilled in the art to achieve optimal labeling conditions. For example, photoincorporation of the photoaffinity probe $8N_3$ATP into GS is preferably elevated by the addition of micromolar levels of $Mn^{2+}$ metal ion. In addition protein concentration can be determinative of the photoresponse. Also, both ammonia and glutamate (co-substrates) enhance photolabelling if $Mg^{2+}$ or $Mn^{2+}$ is present. The higher the protein content of the sample, the denser the solution becomes to light. Therefore, in a denser solution, less UV light reaches the photoreagent per unit of time, decreasing the rate of photoincorporation. Aggregation of the protein can also affect the binding time of the reagent to the protein, thereby increasing or decreasing photoincorporation. One must experimentally redetermine optimal photolysis time when changing protein concentration if maximum incorporation of the photolabel is desired.

By the present invention, it is preferable to photolabel a small 10 to 30 microliter aliquot of cerebral spinal fluid with radioactively-labeled photoaffinity probe (i.e., [$^{32}$P]$2N_3$ATP or [$^{32}$P]$8N_3$ATP) resulting in an approximate final concentration of 10 to 30 $\mu$M for detection of the Alzheimer's disease-specific 42,000 $M_r$ protein. Most preferably, the aliquot of each cerebral spinal fluid analyzed is 15 $\mu$l. However, limits of detection are improved, at little expense, by using larger sample volumes or by concentrating the spinal fluid.

In the alternative, the sample may be labeled with [$^{32}$P]$8N_3$cAMP, in which case the sample is placed on ice to reduce the temperature to about 0° C. and photoactivated. In experiments conducted to evaluate the absence of [$^{32}$P]$8N_3$cAMP photoinsertion into the protein of interest in a cerebral spinal fluid sample, the preferred concentration of [$^{32}$P]$8N_3$cAMP is maintained at not more than 5 $\mu$M.

Detection of the labeled protein occurs following an appropriate, predetermined incubation time to effect a reaction, and is calculated on the basis of the sample and the selected photoaffinity probe.

The intensity of the photolyzing light is such that maximum photoincorporation can be obtained in a minimum amount of time without appreciable change in temperature or damage to the biological sample. Preferably the photolysis is achieved at 254 nm with an ultraviolet light source.

Ultraviolet (UV) light is essential for the activation of the photoprobe treated samples, but only a low intensity UV light is necessary. The intensity of the UV light can range from 180 to 800 $\mu$W/cm$^2$ by conventional sources to 4000 $\mu$W/cm$^2$ and above when a high intensity source is used to achieve rapid photolysis.

Photolysis times range from 15 seconds to 5 minutes and must be experimentally determined for each reaction system. For lamps having intensities of 180–800 $\mu$W/cm$^2$, the preferred photolysis time ranges from approximately 30 to 120 seconds, most preferably, photolysis is effected in approximately 30 to 60 seconds.

The distance of the light source from the sample is a determinative factor in the conditions of photolysis. A preferred method of the present invention uses an ultraviolet light source having sufficient intensity, about 6200 μW/cm², positioned at a set distance, about 1 cm from the sample, for a time sufficient to effect photoactivation, generally approximately 45 seconds.

The labeled macromolecule is typically separated from the solution containing excess unbound sample and/or label by precipitation, although other recognized methods of protein purification are possible. Recognized methods of precipitation include, but are not limited to addition of an effective protein precipitating agent, such as trichloroacetic acid (TCA), perchloric acid (PCA), acetone, ammonium sulfate polyethyleneglycol (PEG) or the like to the sample. PCA or ammonium sulfate are the preferred precipitating agents in the present method, and PCA is the particularly preferred precipitating agent.

The amount of precipitating agent is determined by the concentration of protein in the sample. The preferred concentration of the precipitating agent is that concentration which effectively precipitates the specific protein from solution. The most preferred concentration of the precipitating agent is that amount which effectively precipitates the previously activated, photolabeled cerebral spinal fluid sample.

The precipitating agent can be mixed with the sample as a dry batch addition or in a calculated equivalent liquid form. The required mixing time may vary with the nature of the agent selected and the size or concentration of the sample. However, the time required is that point after which essentially no additional protein is precipitated from the sample solution at the temperature selected.

The precipitated protein may be separated from solution by any effective means, such as centrifugation, sedimentation or filtration. A preferred method of separation of the precipitated protein from the solution is by centrifugation at a sufficient speed and for a sufficient time to effectively isolate the protein into a pellet, for example by centrifugation at 13,000×G for 30 minutes. However, the parameters vary with the nature of the solution.

To determine the effectiveness of the precipitation and separation procedures, both the pellet and the supernatant fluid are analyzed for protein content.

The precipitated protein may be solubilized and any remaining reaction quenched by any effective, known method. The determination of the solubilizing agent would depend on the ultimate method of identifying the specific nucleotide binding protein. Therefore, such agents could include, e.g., sodium dodecyl sulfate (SDS) or urea, and certain stabilizing agents.

Any azide remaining after photolysis may be destroyed by the addition of dithiothreitol or its equivalent, and potential phosphotransfer from the triphosphate derivative $N_3ATP$ or $N_3GTP$ may be inhibited by chelators such as EDTA. The preferred protein solubilizing agent is a detergent, particularly SDS, most preferably in a protein solubilizing mix (PSM), such as described by Potter & Haley in *Meth. in Enzymol.*, 91:613-633 (1983) or by procedures standard to most published procedures. A particularly preferred concentration of SDS in the mix is 10%, resulting in a concentration of SDS to the final sample of 4%.

Solubilization can occur either at 0° C. or at higher temperatures without affecting the results. However, solubilization in the present invention is effective at room temperature.

Upon solubilization, the protein sample is applied to a suitable support for separation of the protein fractions. Support materials could include, e.g., polyacrylamide gels, filter paper, starch gels or blocks, cellulose or polyurethane foam. Any effective, known method of protein separation may be used, but preferably separation is by electrophoresis over denaturing or nondenaturing gels, or over a gradient of either type. In the present method, protein separation is usually by electrophoresis on a denaturing gel.

The nature of the sample and the size of the specific nucleotide binding protein determine the concentration of the gel used, which in turn determines the time for separation and the electrical current which must be applied to best achieve protein separation. The protein fractions of the present invention most preferably may be separated by electrophoresis on an SDS-polyacrylamide gel (SDS-PAGE) or by isoelectric focusing (IEF) or on two dimensional systems (IEF×SDS-PAGE). Typically, the sample is fractionated on a 10% polyacrylamide gel, run over a period of 2½ to 3 hours, with constant amperage of 35 mA and an initial voltage of about 140 volts. Any standard electrophoresis equipment can be utilized.

The resultant gels are exposed to X-ray film and visualized by autoradiography according to methods well known in the art. The gels can also be stained to determine the presence of the unique specific protein band or to ascertain that differences in the amount of photolabel incorporation are not due to drastic changes in the protein levels. Many known protein staining methods are widely recognized, e.g., Coomassie Brilliant Blue R (CBB) or silver staining. CBB is a commonly used stain that detects proteins based on a hydrophobic interaction between the proteins and the dye. Although any available staining method can be used which effectively distinguishes the specific nucleotide binding protein, CBB is the fastest and most economical for the present method.

Most preferably, each completed SDS-PAGE gel is stained with an effective amount of CBB to stain the selected protein fragments. However, many times proteins can be detected by photolabelling that cannot be detected by any protein staining procedure. In particular, the completed gel is immersed in a 10% CBB (w/v) solution for about 1 hour. Then the gel is destained in a solution to effectively remove excess stain. Particularly preferred is a destaining solution of 5% acetic acid and 10% isopropyl alcohol applied for 10-18 hours.

Finally, the specific binding protein fragments may be visualized by standard autoradiography techniques. The use of an intensifying screen effectively accelerates the visualization process of autoradiography. By the method of the present invention, the stained gel is dried, and then exposed to DuPont Cronex 4 X-ray film. The autoradiographic procedure is for variable time periods depending on the specific activity of the probe photoinserted into the proteins of each experimental sample. Alternately, if maintained at −70° C., the gel can be subjected to autoradiographic procedures while still in the gel state.

The amount of protein, as well as the radioactivity incorporated into each protein, can be quantified by known methods including, but not limited to, densitometric scans of the exposed X-ray film, or of the stained gel, or by liquid scintillation spectrometry of the protein band following excision from the gel.

Analyses of cerebral spinal fluid taken from human patients suffering from certain neurological or psychiatric diseases or disorders, when labeled with the appropriate, subsequently activated, radioactive photoaffinity probe, reveals a disease-specific biochemical marker by which an existing disease state can be characterized. For example, a protein band having an apparent molecular weight of about 68,000 D±10% is found in the cerebral spinal fluid of normal human subjects, visualized by a subsequently activated, radioactive photoaffinity probe, e.g., [$^{32}$P]8N$_3$cAMP. More particularly, the identified protein band has an approximate molecular weight of 68 kD. Moreover, a fragment of the same size is recognized in cerebral spinal fluid samples taken from patients afflicted with neurological diseases other than Alzheimer's disease.

By comparison, the cerebral spinal fluid of human patients suffering from Alzheimer's disease, is characterized by an absence of photodetection of the protein fragment having an approximate weight of 68 kD, as visualized by photolabeling by, for example, [$^{32}$P]8N$_3$cAMP (see FIG. 2).

Furthermore, the cerebral spinal fluid of human patients suffering from various neurological and psychiatric disorders, labeled with a subsequently activated, radioactive photoaffinity probe, is found to have unique specific nucleotide binding proteins which can provide a distinctive means of diagnosing particular diseases. For example, a characteristic protein band having an apparent molecular weight of about 42,000 D±10% is found in the radioactive photoaffinity labeled cerebral spinal fluid of Alzheimer's disease patients using [$^{32}$P]8N$_3$ATP. More particularly, the Alzheimer's disease-specific identified protein band has an approximate molecular weight of 42 kD.

By comparison, a systematic survey of the cerebral spinal fluid taken from normal human subjects and labeled with a similar subsequently activated, radioactive photoaffinity probe (i.e., [$^{32}$P]8N$_3$ATP), shows no protein fragment having an approximate weight of 42 kD being photolabeled. Thus, the identified protein is unique to Alzheimer's disease patients. There is apparently no identified corresponding protein fragment contained in the cerebral spinal fluid of normal human subjects.

In addition to being photolabeled with the radioactive photoprobe, the 42,000 M$_r$ protein may be shown to interact with ATP, a naturally occurring nucleotide that is the phosphate donor for many protein kinases and synthetases (last four lanes FIG. 1). Therefore, based on the selectivity, the Alzheimer's disease-specific protein may be identified as an ATP binding protein of about 42,000 M$_r$. Furthermore, the same 42 kD protein can be photolabeled with 8-azido-GTP, defining the specific protein as an ATP and GTP binding protein. However, the 42,000 M$_r$ protein binds ATP with higher affinity.

Therefore, the human cerebral spinal fluid samples can be reliably and accurately distinguished into two groups. The cerebral spinal fluid samples taken from Alzheimer's disease patients show photoinsertion of [$^{32}$P]8N$_3$ATP or [$^{32}$P]2N$_3$ATP into the identified disease-specific 42 kD protein, but an absence of photoinsertion of [$^{32}$P]8N$_3$cAMP in the normal 68 kD protein. Whereas, the samples taken from control subjects, unafflicted by Alzheimer's disease, show photoinsertion of [32P]8N$_3$cAMP into a normal 68 kD protein, but no photoinsertion of either [$^{32}$P]8N$_3$ATP or [$^{32}$P]2N$_3$ATP into a 42 kD protein. The comparative analyses of cerebral spinal fluid samples from Alzheimer's disease patients and from normal human subjects, photolabeled with a GTP analog, confirm the results observed when the 42 kD protein is photo-labeled with the photoaffinity probe of ATP.

Based on mixing experiments of cerebral spinal fluid taken from control subjects (in which the 68 kD protein is photolabeled) and samples of Alzheimer's disease patients' cerebral spinal fluid (in which the 68 kD protein does not photolabel), it may be shown by the present invention that a component of the Alzheimer's disease cerebral spinal fluid apparently prevents photolabeling of the 68 kD protein of normal, control sample cerebral spinal fluid with [$^{32}$P]8N$_3$cAMP.

By the present invention, the Alzheimer's disease-specific 42,000 M$_r$ protein could be further identified as glutamine synthetase. Mammalian glutamine synthetase is an enzyme with 42,000 M$_r$ subunits that catalyzes the following reaction:

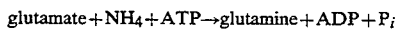

$$\text{glutamate} + \text{NH}_4 + \text{ATP} \rightarrow \text{glutamine} + \text{ADP} + P_i$$

Further, it has been suggested that metabolism of glutamate is altered in Alzheimer's disease (AD) since those sections of the diseased brain which have become dysfunctional show very low levels of glutamate. Moreover, the neuronal cells that die in Alzheimer's disease patients are glutamate sensitive cells.

Glutamine synthetase can also be detected by measuring the enzymatic catalytic conversion of substrates to products. Recognized detection techniques include, for example, measuring the catalytic conversion of [$^{14}$C]glutamate to [$^{14}$C]glutamine or [$\alpha^{32}$P]ATP to [$\alpha^{32}$P]ADP. Such methods of measuring catalytic conversion are applicable to the detection of the Alzheimer's disease-specific 42,000 M$_r$ protein of the present invention.

The 42,000 M$_r$ protein is present in the cerebral spinal fluid of Alzheimer's disease patients in very small quantities. However, other than albumin and a protein of about 28,000 M$_r$, the 42,000 M$_r$ protein is the major protein known to photolabel with either 8N$_3$ATP or 2N$_3$ATP at the concentrations used. Therefore, by using the technique of photoaffinity labeling and the materials and methods of the present invention, it is possible to detect a very minor protein of cerebral spinal fluid that interacts with ATP and GTP, and which appears to be unique in the cerebral spinal fluid of clinically diagnosed Alzheimer's disease patients.

Also important for the diagnosis of other disease states is the dramatic appearance of other smaller molecular weight proteins that photolabel only after filtration. One of these small proteins is tumor necrosis factor (TNF) which is proposed to be elevated in several disease states, including ischemia and AD. Also present is acidic fibroblast growth factor (aFGF). Studies with several different CSFs from neurological diseases show that these proteins change dramatically in different disease states.

Other biological response modifiers (i.e., cytokines, growth factors, etc.) reportedly in this lower molecular weight region of CSF fluids include nerve growth factor (NGF), interleukin-1 (IL-1), interleukin-2 (IL-2), and basic fibroblast growth factor (bFGF). Fluid levels of each of these factors have been postulated to be involved in various disease states. Each of these biological response modifiers, in purified form, are photolabeled with nucleotide photoaffinity probes (Campbell et al, *Proc. Natl. Acad. Sci.* 87:1243-1246 (1990); Mann et at, *Peptide Research* 4:79-83 (1991); Shoemaker et al, *Pro-* tein *Science* 1:884–891 (1992); Doukas et al, *Bioconjugate Chemistry* 3:484–492 (1992); Chavan et at, *J. Biol. Chem.* 267:14866–14870; Trad et al, *Arch. Biochem. Biophys.* 304:58–64 (1993)).

Therefore, the use of the present method leads to a procedure for the diagnosis of diseases by detecting and determining the levels of a collection of small proteins that incorporate photolabel and vary quantitatively and qualitatively depending upon the disease.

A set of studies by the inventor of the present application have permitted the optimization of photo-incorporation into a protein. Thus, it is now possible to label 10–15 microliters of sample with thousands of cpms of $^{32}P$, significantly enhancing the purification of the protein and further improving its value as a diagnostic tool.

Post-mortem studies have shown that the identified 42,000 $M_r$ protein is present in Alzheimer's disease patients photolabels at high levels in the ventricular cerebral spinal fluid, but only at low levels in the lumbar cerebral spinal fluid. However, since the method of the present invention advantageously permits identification and purification of the specific nucleotide binding protein from only minute microliter amounts of cerebral spinal fluid, the labeled 42 kD protein can be detected in samples containing only very low levels of the protein. Additionally, recent results using 1 ml aliquots of lumbar cerebral spinal fluids treated to 40% ammonium sulfate saturation gave a protein precipitate that contained easily detectable amounts of the 42,000 $M_r$ protein on photolabeling with $[^{32}P]2N_3ATP$. This confirms that lumbar cerebral spinal fluid can be used in this diagnostic test.

Figure 4:
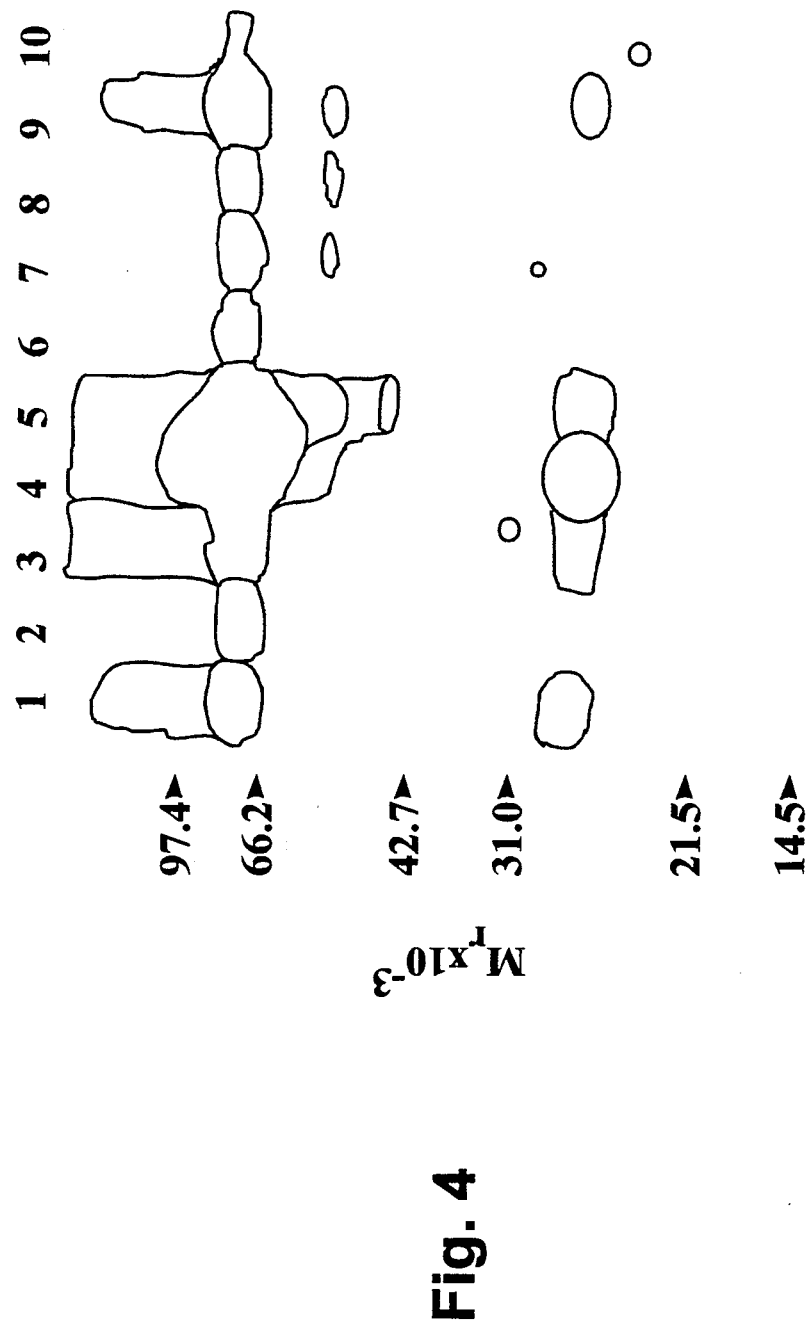
FIG. 4 is a photograph of an autoradiograph made from an SDS-PAGE on which human cerebral spinal fluid proteins from Amyotrophic Lateral Sclerosis (ALS or Lou Gehrig's disease) or Alzheimer's Diseased (AD) patients were separated after photolabeling with $[^{32}P]8N_3ATP$ or $[^{32}P]8N_3GTP$. This autoradiograph shows that neither $[^{32}P]8N_3ATP$ or $[^{32}P]8N_3GTP$ detects the AD specific 42,000 $M_r$ protein in the cerebral spinal fluid of patients with ALS. This further confirms the selectivity of this approach as a diagnostic test for AD. However, using $[^{32}P]8N_3GTP$ a protein of about 55,000 $M_r$ is photolabeled in only the ALS cerebral spinal fluid. Further tests indicate that this protein is only found in the cerebral spinal fluid of ALS patients and is probably diagnostic of this disease.

By a similar procedure, a protein band having an apparent molecular weight of about 55,000 D is found in the cerebral spinal fluid of amyotrophic lateral sclerosis (ALS or Lou Gehrig's disease) patients, visualized by a subsequently activated, radioactive GTP photoaffinity probe. Moreover, the unique ALS-specific 55,000 $M_r$ protein is not found in the cerebral spinal fluid of either normal subjects or patients with Alzheimer's disease as shown in FIG. 4.

By another similar procedure, blood serum proteins having an apparent molecule weight of 120 kD, 31 kD, 24 kD and 14–16 kD show altered labelling among normal patients and patients with sickle cell anemia, leukemia or lung cancer.

Therefore, the unique variations in the pattern of photolabeled protein fragments found in a small sample of a patient's cerebral spinal fluid or serum provides the key to identifying an existing disease state affecting the patient. The compositions, methods, and test kits of the present invention, when applied to minute amounts of cerebral spinal fluid sample, can photolabel and detect the disease-specific biochemical marker by which a particular disease state may be identified in a patient.

The novel method of the present invention incorporates a dual system of comparison in order to diagnose the disease state. It is not enough that a specific disease state is recognized simply by the apparent absence of a specific protein. A conclusion based on only the absence of a result could prove erroneous. For example, the protein could actually be present, but not properly photolabeled because of procedural errors.

By the present invention the diagnosis may be based on both the presence of a unique disease-specific binding protein or biochemical marker in a sample of body fluid from a diseased patient, and the absence of a "normal" binding protein or biochemical marker characteristically found in samples from normal subjects. Therefore, the present inventive method has met a long-felt need in the art for a reliable, accurate, safe and effective method which distinguishes Alzheimer's disease patients from both normal subjects and patients afflicted with other neurological or psychiatric disorders or dementias, and which distinguishes patients with various other disease states from each other and from normal patients. Moreover, the invention advantageously has also met the equally long-felt need for a reliable, accurate, safe and effective method to detect disease-specific biochemical markers for other neurological syndromes or diseases, such as ALS, in a patient so afflicted.

In order that those skilled in the art can more fully understand the present invention and advantages thereof, the following examples are set forth. These examples are given solely for the purpose of illustration, and should not be considered as expressing limitations unless so set forth in the appended claims.

EXAMPLES

Standard procedures and reagents were used in accordance with Maniatis et al. (1982) *Molecular Cloning: A Laboratory Manual*, Cold Spring Harbor Laboratory, New York. Specific techniques for the photoaffinity labeling of specific nucleotide binding sites with purine phosphate azide analogs were used in accordance with Potter & Haley, *Meth. in Enzymol.*, 91:613–633 (1983). Approximate molecular weights were represented as migration rates ($M_r$) values as estimated from plots of the migration rate versus the log molecular weight of commercial protein standards. Each sample was analyzed at least three times to ensure accurate results.

Example 1—Purification of the Cerebral Spinal Fluid Protein

The diagnostic proteins of the present invention were characterized using the results of blind assays of cerebral spinal fluid samples from 40 patients having conditions diagnosed as Alzheimer's disease, Parkinson's disease or epilepsy, and corresponding age matched controls.

The cerebral spinal fluid samples were stored at −20° C. for various periods of time without adversely affecting the experiments. Experiments conducted on fleshly collected and immediately photolabeled cerebral spinal fluid displayed the same characteristics as frozen samples stored for extended periods of time. Fresh cerebral spinal fluid samples were collected from cadavers within a few hours of death. Frozen samples were shipped on dry ice from suppliers, Eli Lilly, Inc. and Athena Neurosciences, then stored at −20° C. until assayed. For each experiment, the sample was thawed completely, an aliquot was withdrawn, then the sample was immediately refrozen and returned to −20° C. storage. Samples were handled with gloved hands at all times.

Each assay was performed on 15 $\mu l$ of cerebral spinal fluid. Although the amount of cerebral spinal fluid tested remained constant for each experiment, the protein concentration of each sample varied to some degree. However, the slight protein variation showed no effect on the outcome of the experiment.

Occasionally, lumbar cerebral spinal fluid samples from some Alzheimer's disease patients contained too little of the 42,000 $M_r$ protein to be visualized. Those samples were concentrated using vacuum procedures, lyophilization or Speed-vac concentration, prior to photolysis or by precipitation of proteins by ammonium sulfate or polyethylene glycol or the like.

Concentration increased the visibility of the 42,000 $M_r$ protein in cerebral spinal fluid samples from Alzheimer's disease patients, but did not make the corresponding 42,000 $M_r$ protein band detectable in the cerebral spinal fluid from normal, control subjects. Moreover, following the vacuum concentration procedure, the 68,000 $M_r$ proteins no longer photolabeled with [$^{32}$P]8N$_3$ATP. However, the effect was shown not to be generalized since photolabeling of the 26,000 $M_r$ protein, apparently present in all cerebral spinal fluid samples, did not decrease following vacuum concentration. As a result, the 42,000 $M_r$ protein was more readily visible since it was one of only two major photolabeled species. Usually 1 ml of the cerebral spinal fluid sample was evaporated under vacuum conditions to a final volume of about 0.2 to 0.3 ml, resulting in an increased detection of the 42,000 $M_r$ protein of about 3- to 5-fold. Ammonium sulfate precipitation of 40% saturation of a 1 ml aliquot of lumbar cerebral spinal fluid increased detection at least 10 to 20 fold.

Each cerebral spinal fluid sample was photolabeled with [$^{32}$P]8N$_3$ATP to identify the 42,000 $M_r$ protein. The cerebral spinal fluid sample was comprised of cerebral spinal fluid, buffer, and water. The photoprobes used in each experiment were prepared by the inventor according to the procedures disclosed by Potter and Haley in *Meth. in Enzymol.*, 91:613–633 (1983). Probes were also available commercially through ICN Radiochemicals 2727 Campus Drive, Irvine, Calif. 92715.

Several concentrations of [$^{32}$P]8N$_3$cAMP were used in the various experiments. The concentrations varied from 1 $\mu$M to 10 $\mu$M, but produced no significant variation in the results. Photo-labeling differences were most apparent at low concentrations of [$^{32}$P]8N$_3$cAMP with the Alzheimer's disease 68,000 $M_r$ protein, wherein the degree of photoinsertion was much less than that of the comparable control 68,000 $M_r$ protein. The decreased availability of the 68,000 $M_r$ protein in Alzheimer's disease patient samples is very concentration dependent, with virtually no observable photoinsertion below a 5 $\mu$M concentration of [$^{32}$P]8N$^3$cAMP.

In each experiment, photoprobe was added to the cerebral spinal fluid sample and vortexed for 6 seconds. Each treated sample was then allowed to mix for an additional 24 seconds at room temperature before exposure to ultraviolet (UV) light.

The treated samples were placed on ice and exposed to UV light for 45 seconds. The UV light source, a hand-held UV lamp with an intensity of 6200 $\mu$W/cm$^2$, was positioned 1 cm from the sample. The UV activation of the photoprobe labeled samples was always conducted at 0° C.

The samples were precipitated by the addition of 6% perchloric acid or by the addition of increasing amounts of ammonium sulfate. Precipitation by ammonium sulfate was used to purify the protein for further characterization of the protein found in the Alzheimer's disease cerebral spinal fluid or for antibody production. The protein precipitated by each ammonium sulfate addition was saved for electrophoretic analysis and autoradiography.

The percentage of ammonium sulfate that precipitated the identified protein was sufficiently specific that it was used as a factor to characterize the protein and its properties. Therefore, by combining the ammonium sulfate precipitations from before and after photolabeling, the 42,000 $M_r$ protein was concentrated from large volumes of cerebral spinal fluid. Simultaneously, most of the contaminating proteins were removed.

The 42,000 $M_r$ protein was precipitated by a 40% ammonium sulfate saturation. The calculated amount of solid ultrapure ammonium sulfate necessary to result in 40% saturation was added to each previously activated, photolabeled cerebral spinal fluid sample. The mixture was stirred gently for 30 minutes at room temperature, then centrifuged in a table top centrifuge (13,000×G) for 30 minutes to separate the purified protein. Small aliquots of each supernatant and pellet were analyzed for protein content by SDS-PAGE.

The purified protein samples were solubilized in a protein solubilizing mix (PSM), standard to most published procedures. The concentration of SDS (sodium dodecyl sulfate) in the mix was 10%, resulting in a concentration of SDS to the final sample of 4%. Samples were solubilized in each experiment at room temperature.

Each sample was fractionated by 10% SDS-PAGE, run over a period of 2½ to 3 hours, with constant amperage of 35 mA and an initial voltage of 140 volts. Since all of the proteins were very well separated on a 10% gel, a gradient was not necessary.

The completed SDS-PAGE gels were stained to detect the protein before exposing the gel to X-ray film. Coomassie Brilliant Blue R (CBB) proved to be the fastest and most effective stain for protein detection in these experiments. Each completed SDS-PAGE gel was stained with a 10% CBB (w/v) solution for about 1 hour, then destained in a solution of 5% acetic acid and 10% isopropyl alcohol for 10–18 hours, then washed three times to remove that portion of the photoaffinity label which had not crosslinked with the specific nucleotide binding protein.

Finally, the stained gels were dried and exposed to DuPont Cronex 4 X-ray film. The autoradiographic procedure involved variable time periods depending on the specific activity of the probe photoinserted into the proteins of each experimental sample, and the presence of an intensifying screen to accelerate visualization of the specific protein band.

The quantity of protein, as well as the amount of the radioactivity incorporated into each protein, was quantified by densitometric scans of the exposed X-ray film, or of the stained gel, or by liquid scintillation spectrometry of the protein band excised from the gel. Significance was determined by analysis of variance at a rho level below 0.50.

From among the 40 samples analyzed under blind conditions, all 16 cerebral spinal fluid samples from Alzheimer's disease patients showed photo-insertion by [$^{32}$P]8N$_3$ATP into the 42,000 $M_r$ protein. By comparison, only two "control" samples showed photoinsertion into the 42,000 $M_r$ protein, but the samples were from subjects aged 86 & 94, who had not been identified as free of Alzheimer's disease. Only 3 samples, each provided by the same laboratory, failed to demonstrate photoinsertion as expected. Furthermore, the specific 42,000 $M_r$ protein was found absent in the remaining 19 cerebral spinal fluid samples, consisting of about equal numbers of samples from control subjects or from patients affected by Parkinson disease or epilepsy.

Example 2—Photolabeling of Cerebral Spinal Fluid Samples with [γ$^{32}$P]8N$_3$ATP Comparative cerebral spinal fluid samples were obtained from Athena Neurosciences from patients known to have epilepsy (lane E), Parkinson's disease (lane P) or Alzheimer's disease (AD), or from normal control subjects (lane N) as shown in FIG. 1. The samples were processed, photolabeled with [γ$^{32}$P]8N$_3$ATP and analyzed according to the procedures of Example 1. However, as shown in the FIG. 1 photograph of the autoradiograph of an SDS-PAGE gel on which the proteins in the cerebral spinal fluid samples were screened in a blind manner, a protein of about 42 kD was photolabeled only in the samples from Alzheimer's disease patients.

Example 3—Photolabeling of Cerebral Spinal Fluid Samples with [$^{32}$P]8N$_3$CAMP The comparative cerebral spinal fluid samples were the same as those used in Example 2, from patients known to have epilepsy (lane E), Parkinson's disease (lane P) or Alzheimer's disease (AD), or from normal control subjects (lane N) as shown in FIG. 2. The samples were processed, photolabeled with [$^{32}$P]8N$_3$cAMP and analyzed according to the procedures of Example 1.

As shown in FIG. 2, two matched SDS-polyacrylamide gels (FIG. 2C and FIG. 2D) were run to separate the cerebral spinal fluid proteins in each sample after photolabeling with [$^{32}$P]8N$_3$cAMP. Gel I was stained with CBB (FIG. 2C), then exposed to X-ray film and analyzed by autoradiography (FIGS. 2A and 2B, top). Gel II was stained (FIG. 2C) analyzed by autoradiography (FIGS. 2A and 2B, bottom).

The CBB stained gel (FIGS. 2C and 2D) showed that there were several proteins found in the cerebral spinal fluid. The protein levels did not change when comparisons were made between Alzheimer's disease and control samples. However, by comparison, the autoradiographs (FIGS. 2A and 2B, top & bottom) show that the amount of [$^{32}$P]8N$_3$cAMP photolabel incorporated into each protein did vary between Alzheimer's disease and control samples. Notably, more bands appeared on the stained gel than on the exposed X-ray film because not all cerebral spinal fluid proteins were subject to photoinsertion. As shown in FIG. 2, a protein of about 68 kD was photolabeled only in the samples from patients diagnosed as not having Alzheimer's disease. In contrast, as shown in FIG. 1, a protein of 42 kD was photolabeled with [$^{32}$P]8N$_3$ATP only in samples from Alzheimer's diseased patients.

The differences between the stained gel and the exposed autoradiographic film demonstrated that photolabeling of a protein is a very specific and reproducible process. The experiments have shown that each photolabeled disease-specific protein band has essentially the same M$_r$ value, with slight variations due only to minor variations in the gel itself.

Example 4—Purification of the Alzheimer's Disease-Specific 42 kD Binding Protein The 42 kD cerebral spinal fluid protein was isolated as a pure fraction by the following high performance liquid chromatography (HPLC) procedure. The cerebral spinal fluid from Alzheimer's disease patients was photolabeled and the protein fraction was precipitated by ammonium sulfate at 20 to 40% saturation. The precipitated proteins were solubilized in Buffer A [0.1% trifluoroacetic acid (TFA)] and subjected to HPLC on a C4 column with the following acetonitrile gradient: 0–20 minutes at 0% buffer B; then 20–80 minutes at increasing percentages of buffer B to 100%, wherein buffer B was 0.1% TFA and 70% CH$_3$CN (acetonitrile).

The 42 kD protein was eluted at approximately 82–92% B. The fraction was also radioactive if the sample was photolyzed with [$^{32}$P]2N$_3$ATP or [γ-$^{32}$P]8N$_3$ATP prior to the ammonium sulfate precipitation. The purity and identity of the fraction was confirmed by SDS-PAGE of the fraction and autoradiographic visualization. Therefore, it was concluded that the purified protein was subject to photoinsertion and had a molecular weight of 42,000 D.

Example 5—Identification of the Alzheimer's Disease-Specific 42,000 M$_r$ Protein Found in Cerebral Spinal Fluid Based on the following evidence, the Alzheimer's disease-specific 42 kD protein detected by the method of the present invention in the photoaffinity labeled cerebral spinal fluid from Alzheimer's disease patients is mammalian glutamine synthetase (GS).

1. Purified GS (purchased from Sigma, purified from sheep brain) comigrated on SDS-PAGE identically with the 42,000 M$_r$ protein in the cerebral spinal fluid from Alzheimer's disease patients.

2. Purified GS and the 42 kD protein found in the cerebral spinal fluid from Alzheimer's disease patients had the same approximate saturation and Kd values for binding ATP, 8-azido-ATP and 2-azido-ATP. That is, both proteins showed saturation of photoinsertion by 40–50 μM with half maximal photoinsertion occurring at about 10 μM with both 2-azido-ATP and 8-azido-ATP. Also, ATP decreased the photolabeling of both proteins, with either 8- or 2-azido-ATP, at nearly identical concentrations of ATP. Therefore, both GS and the 42 kD protein in the cerebral spinal fluid from Alzheimer's disease patients had the same nucleotide binding properties.

3. Photolabeling of purified GS and the 42 kD protein found in the cerebral spinal fluid from Alzheimer's disease patients exhibited the same kinetic properties upon addition of certain ligands known to affect the kinetics of GS with regards to binding of nucleotides as shown in FIG. 3. More specifically, the addition of 100 mM ammonium bicarbonate enhanced the binding of [$^{32}$P]2N$_3$ATP, and therefore the photolabeling of both the 42 kD cerebral spinal fluid protein and GS, by about 5-fold. Also, addition of 10mM glutarate (a glutamate substrate analog) slightly decreased the binding of [$^{32}$P]2N$_3$ATP, and therefore slightly decreased the photolabeling of both the 42 kD cerebral spinal fluid protein and GS in the presence of excess ammonium bicarbonate.

4. A nearly identical mole to mole ratio of photoinsertion was noted with both GS and the cerebral spinal fluid 42 kD protein from Alzheimer's disease patients. Both proteins showed the same relative photoinsertion efficiencies of 8-azido-ATP versus 2-azido-ATP. In particular, the amount of photo-incorporation into both GS and the 42 kD protein found in the cerebral spinal fluid from Alzheimer's disease patients was greater on a mole to mole basis when [γ$^{32}$P]2N$_3$ATP was used as a photolabel, rather than the structurally different ATP analog [γ$^{32}$P]8N$_3$ATP.

5. Both purified GS and the 42 kD protein found in the cerebral spinal fluid from Alzheimer's disease patients were labeled with a secondary radioiodinated-antibody known to be reactive to an antibody selective for GS (rat brain) in a Western blot. However, other cerebral spinal fluid proteins and creatine kinase did not crossreact with this GS antibody. Therefore, antibody selective for GS also reacted with the 42 kD protein of the cerebral spinal fluid from Alzheimer's disease patients.

6. The elution pattern of both the 42 kD protein and purified GS was nearly identical on HPLC chromatography using a C4 column and acetonitrile gradient as described in Example 4. Both eluted at about 75–85% buffer B.

7. On 2-dimensional gel electrophoresis (IEF×SDS-PAGE) the 42 kD protein in the cerebral spinal fluid from Alzheimer's disease patients was a single species, having a pI value of 6.0±0.2 pH units. By comparison, with the purified GS from Sigma the pI range of the major protein species at 42,000 $M_r$ value was 5.8–7.2 and consisted of 6 isoelectric forms. The most acidic of the isoelectric forms migrated on 2-dimensional gels identically with the 42 kD photolabeled protein in the cerebral spinal fluid from Alzheimer's disease patients.

Example 6—Development of an Immunoassay for the Disease-Specific Alzheimer's Disease Protein Levels of GS in brain homogenates from both normal, control subjects and Alzheimer's disease patients were assayed in terms of immunological response to a GS antibody. GS was determined to be greatly elevated in the samples from Alzheimer's disease patients in comparison to the control samples.

By the presently claimed method, it will be possible to isolate and purify the 42,000 $M_r$ protein for the specific production of both polyclonal and monoclonal antibodies. Furthermore, since the 42,000 $M_r$ protein is glutamine synthetase with a specific substrate, it will be possible to develop a biochemical assay for the presence of this enzyme based on GS's catalytic properties.

A reliable diagnostic test for Alzheimer's disease requires the purification and identification of the specific protein unique to Alzheimer's diseased patients. In particular, polyclonal and monoclonal antibodies against GS facilitate detection by immunmoassay. A monoclonal antibody directed to sheep brain GS (SBGSAb) specifically detected the GS protein in CSF of Alzheimer's Disease patients.

Example 7—Photolabeling of Cerebral Spinal Fluid Samples from Amyotrophic Lateral Sclerosis and Alzheimer's Disease Patients Cerebral spinal fluid samples from 4 patients known to have amyotrophic lateral sclerosis (lane ALS) were compared with samples from patients with Alzheimer's disease (lanes AD). Each sample was processed, photolabeled with $[\gamma^{32}P]8N_3ATP$ or $[\gamma^{32}P]8N_3GTP$ and analyzed according to the procedures of Example 1.

As shown in the FIG. 4 photograph of the autoradiograph of an SDS-PAGE gel on which the proteins in the cerebral spinal fluid samples were screened, a specific protein of about 55,000 $M_r$ was photolabeled with $[\gamma^{32}P]8N_3GTP$ only in the cerebral spinal fluid samples from ALS patients. The 55,000 $M_r$ radiolabeled band was visible in each of the four samples of $[^{32}P]8N_3GTP$ photolabeled cerebral spinal fluid from ALS patients.

Although the $[^{32}P]8N_3GTP$ photolabeled bands shown in FIG. 4, ALS #1, appeared to be about 1/12 as intense as the corresponding protein bands in FIG. 4, lanes 2, 3 and 4, it was nevertheless detectable.

By comparison, the $[^{32}P]8N_3GTP$ photolabeled 55 kD protein was not observed in cerebral spinal fluid samples from Alzheimer's disease patients or from several other non-ALS subjects. Moreover, no detectable photoinsertion into the Alzheimer's disease-specific 42 kD protein was found in the cerebral spinal fluid samples from ALS patients. Therefore, the present method of photoaffinity labeling with nucleotide affinity probes to identify unique disease-specific proteins in the patient's cerebral spinal fluid was shown to be effective in the determination of the presence or development of certain human neurological diseases or syndromes.

Figure 5B:
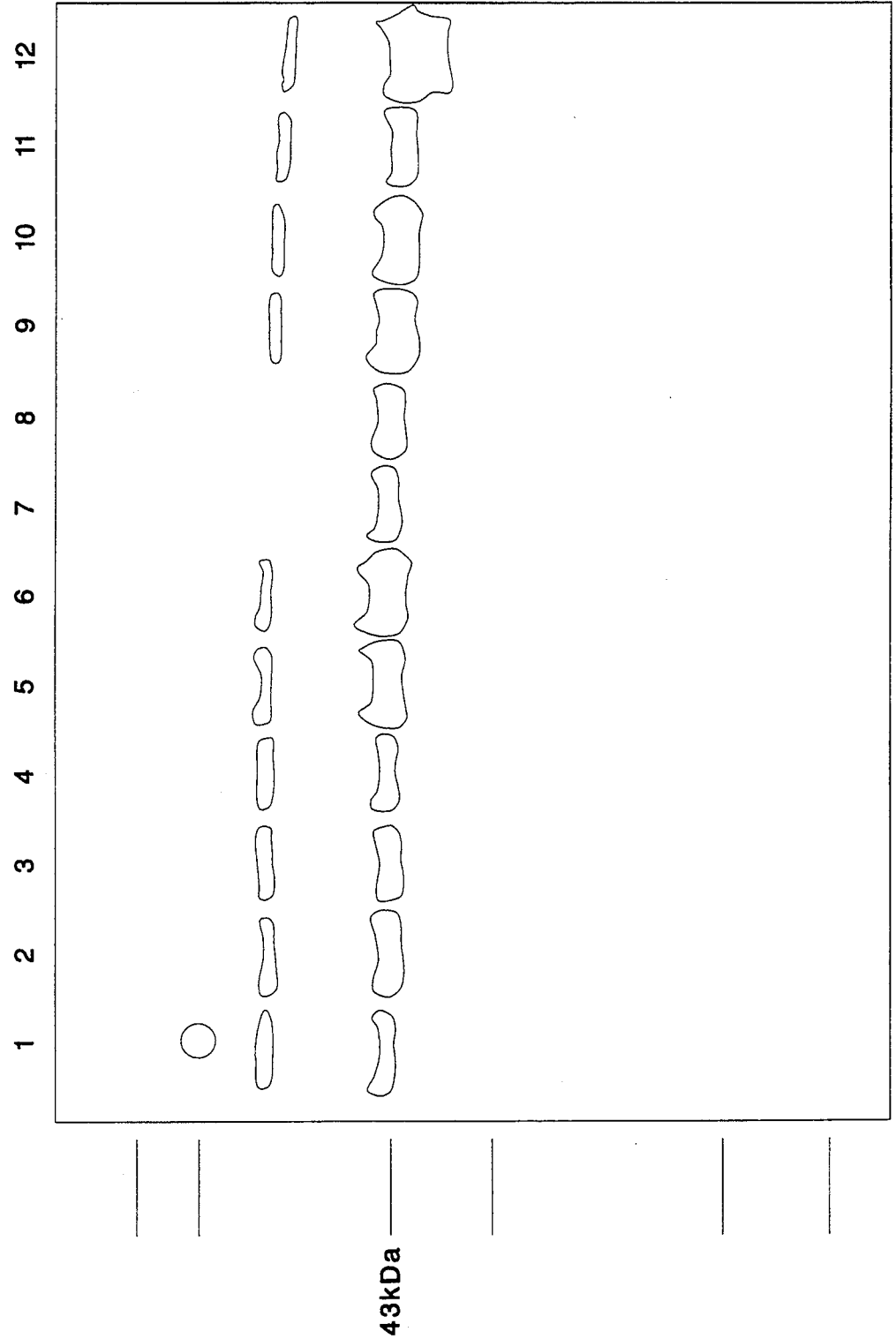
FIG. 5B is an autoradiograph of the SDS-PAGE gel of FIG. 5A which shows that the presence of $Mn^{2+}$ greatly enhances the photolabelling of GS by $[^{32}P]8N_3ATP$.

Example 8—Photolabeling of Purified Glutamine Synthetase Under Various Conditions Purified glutamine synthetase from sheep brain was photolabeled by the above-described method, but under various ionic conditions. FIG. 5A is the SDS-PAG demonstrating GS bands, and FIG. 5B is the autoradiograph illustrating the effect of ionic conditions on photoinsertion of the $8N_3\alpha$-ATP photolabel.

The conditions in FIG. 5 are as follows:
lane 0: markers (note that purified GS runs at approximately the 43 kD marker
lane 1: Tris-HCl buffer
lane 2: $Mg^{2+}$ (100 µM)
lane 3: $NH_4^+$ (10 mM)
lane 4: Glutamate (200 µM)
lane 5: $Mn^{2+}$ (10 µM)
lane 6: $Mg^{2+}$ (100 µM), $Mn^{2+}$ (10 µM)
lane 7: $Mg^{2+}$ (100 µM), $NH_4^+$ (10 mM)
lane 8: $Mg^{2+}$ (100 µM), Glutamate (200 µM)
lane 9: $Mg^{2+}$ (100 µM), $Mn^{2+}$ (10 µM), $NH_4^+$ (10 mM)
lane 10: $Mg^{2+}$ (100 µM), $Mn^{2+}$ (10 µM), Glutamate (200 µM)
lane 11: $Mg^{2+}$ (100 µM) $NH_4^+$ (10 mM), Glutamate (200 µM)
lane 12: $Mg^{2+}$ (100 µM) $NH_4^+$ (10 mM), Glutamate (200 µM), $Mn^{2+}$ (10 µM).

As is evident from FIG. 5, photolabeling increases dramatically in all lanes where $Mn^{2+}$ (by adding $MnCl_2$) is present. The level of photoinsertion is best under the conditions of lane 12, namely, $Mg^{2+}$ (100 µM), $NH_4^+$ (10 mM), Glutamate (200 µM), $Mn^{2+}$ (10 µM). $MnCl_2$ at 10 µM also increases the enzymatic activity of glutamine synthetase.

Example 9—Enhancement of Photolabeling of GS and Four Other Proteins in CSF Samples by Centricon Filtration CSF samples from AD patients at an early stage of the disease were filtered using a Centricon filter unit according to manufacturer's instructions. Briefly, 200 µl of CSF was added to a Centricon filter unit, and the unit was centrifuged at 9000 rpm for 15 minutes to a volume of 40 µl. The filtered CSF was then brought back to 200 µl total volume and subjected to photolabeling as described above.

Figure 6A:
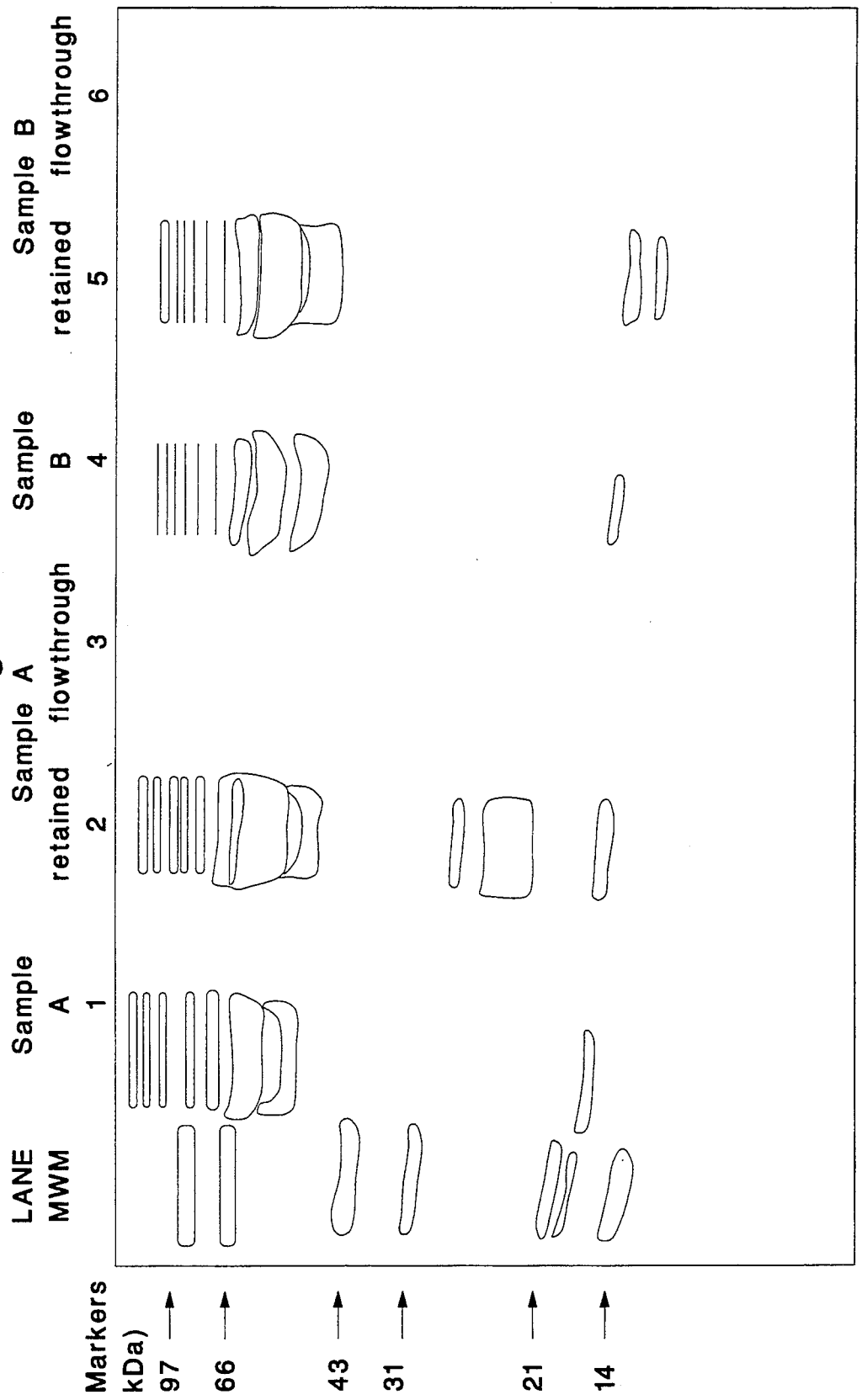
FIG. 6A is an SDS-PAGE gel demonstrating photolabeling of two samples from patients in an early stage of AD.

FIG. 6A is a stained SDS-PAG showing that CSF proteins are present at roughly equal levels in (a) the whole CSF and in (b) the CSF filtered to remove small molecular weight compounds then brought to original volume. In lanes 1 and 4 was run whole CSF (lumbar)

from patients with AD in early stages. In lanes 2 and 5 are filtered CSF proteins. Lanes 3 and 6 contain the flow-through which contains no proteins but does contain small molecules which interfere with photolabeling.

FIG. 6B is an autoradiograph of the gel of FIG. 6A, which shows the increase in photolabeling of the same CSFs after Centricon filtration which removes small molecules that interfere with photolabeling. It can be seen that GS is photolabeled in all lanes that contain CSF proteins (i.e., lanes 1, 2, 4 and 5). GS photolabeling increases in CSF that has been filtered (compare lanes 1 and 4 with 2 and 5 at the 43 kD region). Filtration also increases the photolabeling of several proteins in the range of 28,000 to 6,000 daltons. One protein which is photolabeled as a 17 kD band co-migrates with TNF. Nothing in the flow-through lanes photolabels.

It can be seen from the figure that the glutamine synthetase band at 43 kD is much easier to detect after filtration. This greatly improves the photolabeling technique as a diagnostic aid for AD and other diseases that may result in elevated glutamine synthetase in the CSF.

Figure 7:
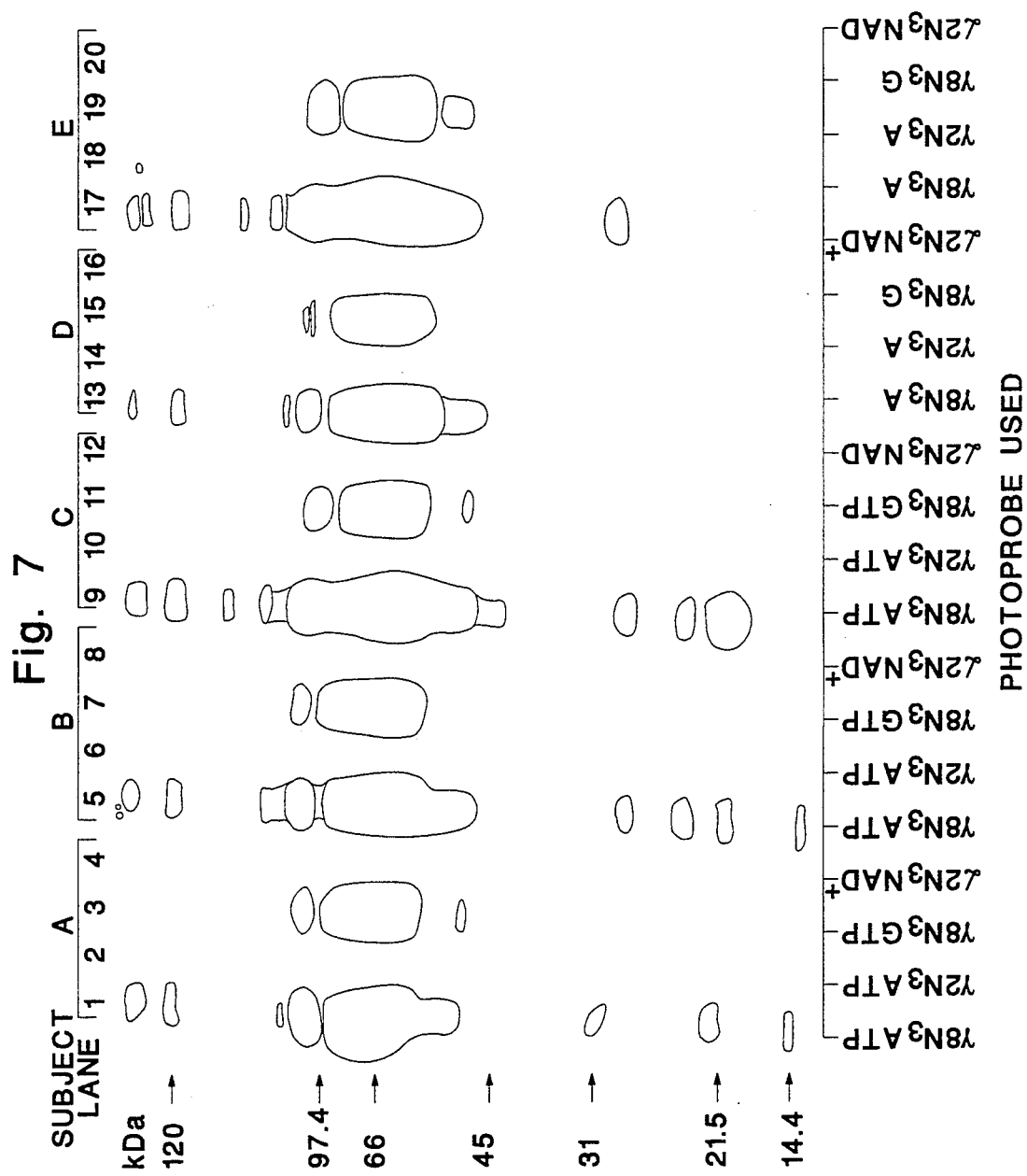
FIG. 7 is an autoradiograph made from an SDS-PAG on which photolabeled proteins from blood serum of normal, sickle cell anemia and cancer patients were separated.

Example 10—Labelling of Specific Serum Proteins for Aiding in the Diagnosis of Cancer and other Diseases A 5 μl serum sample from two normal patients (subjects A and B, lanes 1-4 and 5-8 of FIG. 7, respectively), from a patient with suppressed leukemia (subject C, lanes 9-12), a patient with sickle cell anemia (subject D, lanes 13-16) and a patient with lung cancer (subject E, lanes 17-20) were photolysed in the presence of 40 micromolar of one of the four nucleotide photoaffinity probes indicated in FIG. 7, and subjected to SDS-PAGE.

The Coomassie blue stained protein profile showed little difference among these patients. However, the autoradiograph showed several significant differences. For example, comparing lanes 1, 5, 9, 13 and 17 photolabeled with [$^{32}$P]8N$_3$ATP: (i) subjects A, B and D show lighter photolabeling of a 120 kD protein whereas the two cancer patients show increased photolabeling; (ii) subjects A, B and E show photolabeling of a 31 kD protein whereas none is observed in subjects C and D; (iii) subjects A and B (normals) show light labeling of a protein at about 24 kD whereas very heavy photolabeling is observed in the leukemia subject C and no photolabeling is observed in subjects D and E; (iv) subjects A, B and D show photolabeling of a 15 kD protein whereas subjects C and E show no photolabeling. These differences can be quantified using an ambis 4000 2-D Imaging system.

A longer exposure of the SDS-PAG to film showed that non-cancer patients had [$^{32}$P]8N$_3$GTP photolabeled proteins of 24 and 14 kD that were not present in subjects C and E. Also, cancer patients C and E showed higher photolabeling with [$^{32}$P]2N$_3$ATP of a protein of 16 kD that was only lightly photolabeled in the A, B and D non-cancer subjects. No differences between patients were seen with the [$^{32}$P]2N$_3$NAD+ probe.

Example 11—Changes in Photolabeling of Specific Serum Proteins Following Centricon Filtration 200 μl of serum from the patients described in Example 10 were spun in a Centricon filtration tube to a volume of about 40 μl. One ml of buffer consisting of 10 mM phosphate, 2 mM EDTA and 1 mM MgCl$_2$ at pH 7.0 was added and the spin filtration repeated until a volume of 40 μl was left. The volume was then adjusted back to the original 200 μl with 10 mM phosphate and 1 mM MgCl$_2$ at pH 7.0.

Figure 8:
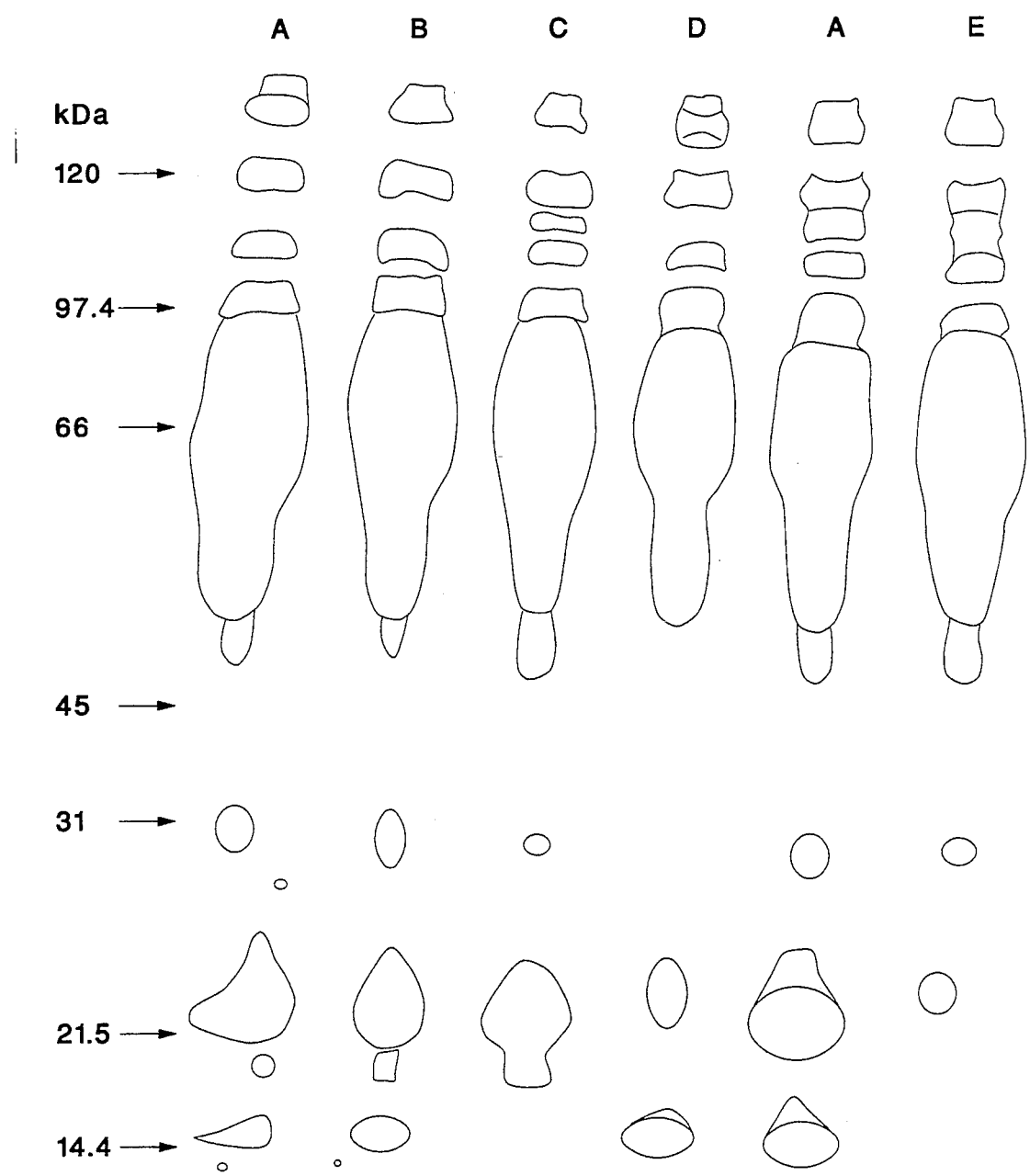
FIG. 8 is an autoradiograph made from an SDS-PAG on which photolabeled proteins from blood serum of normal and cancer patients were separated subsequent to spin filtration. Significant changes were observed in the level of photolabelling of several proteins especially those below 40,000 $M_r$ values.

FIG. 8 is an autoradiograph made from an SDS-PAG on which the photolabeled, filtered samples were run. A major change in photolabeling of the 24 kD protein was seen in the normal subjects A and B with levels approaching that seen in the leukemia patient (subject C). However, subjects D and E still did not photolabel. This indicates that subjects A and B have a small molecule in their serum that blocks photolabeling of the 24 kD protein whereas subject C does not have this small molecule and photolabels quite well with or without filtration. Also, subjects D and E appear not to have this protein at detectable levels in their serum. Further differences are seen at 15 kD where subjects C and E again show no photolabeling. The 120 kD protein now shows equal labeling in all subjects. Other less noticeable differences were observed between these patients which may also be important, for example at about 31 kD.

Although the present invention has been described with reference to the presently preferred embodiment, it should be understood that the skilled artisan may make various modifications, substitutions, omissions, and changes without departing from the spirit of the invention. Accordingly, it is intended that the scope of the present invention be limited only by the scope of the following claims, including equivalents thereof.

What is claimed is:

1. A method for aiding in the diagnosis of Alzheimer's disease in a mammal, comprising:
    a) contacting in the presence of micromolar levels of Mn$^{2+}$ ion a cerebrospinal fluid sample which contains a nucleotide binding protein having an apparent M$_r$ of about 42,000 daltons, wherein said protein is glutamine synthetase, with an effective amount of a labeled ATP- or GTP-analog photoaffinity-labeling reagent which specifically binds said nucleotide binding protein at the nucleotide binding site to photoaffinity label said nucleotide binding protein;
    b) fractionating said cerebrospinal fluid sample to separate the photoaffinity-labeled nucleotide binding protein;
    c) detecting the presence of the separated photoaffinity-labeled nucleotide protein; and
    d) correlating the presence of the photoaffinity-labeled nucleotide binding protein to the presence of Alzheimer's disease.

2. The method for aiding in the diagnosis of Alzheimer's disease according to claim 1, wherein the labeled photoaffinity labeling reagent is radioactively labeled.

3. The method for aiding in the diagnosis of Alzheimer's disease according to claim 1, wherein the photoaffinity labeling reagent is activated by an ultraviolet light sufficient to effect photoactivation.

4. The method for aiding in the diagnosis of Alzheimer's disease according to claim 1, wherein the solubilized photoaffinity-labeled protein is separated by gel electrophoresis.

5. The method for aiding in the diagnosis of Alzheimer's disease according to claim 1, wherein the radioactively labeled photoaffinity labeling reagent is [$^{32}$P] 8-azidoadenosine-5'-triphosphate ([$^{32}$P]8N$_3$ATP) or [$^{32}$P]2-azidoadenosine-5'-triphosphate ([$^{32}$P]2N$_3$ATP).

6. The method for aiding in the diagnosis of Alzheimer's disease according to claim 1, in a patient afflicted with Alzheimer's disease, wherein the sample contains no detected [$^{32}$P]8N$_3$cAMP photolabeled protein at an apparent M$_r$ of about 68,000 daltons.

7. A method for aiding in the diagnosis of Alzheimer's disease in a mammal, comprising:
   a) contacting in the presence of micromolar levels of Mn$^{2+}$ ion a sample of cerebrospinal fluid from a mammal which contains a nucleotide binding protein having an apparent M$_r$ of about 42,000 daltons with an effective amount of a labeled ATP- or GTP-analog photoaffinity-labeling reagent which specifically binds said nucleotide binding protein at the nucleotide binding site to photoaffinity label said nucleotide binding protein;
   b) precipitating the photoaffinity-labeled protein from the sample using an effective amount of a precipitating agent;
   c) solubilizing the precipitated photoaffinity-labeled protein;
   d) subjecting the solubilized photoaffinity-labeled protein to electrophoresis to separate the photoaffinity-labeled protein;
   e) detecting the presence of the separated photoaffinity-labeled protein; and
   f) correlating the presence of the photoaffinity-labeled protein to the presence of Alzheimer's disease.

8. The method for aiding in the diagnosis of Alzheimer's disease according to claim 7, wherein the labeled photoaffinity labeling reagent is radioactively labeled.

9. The method for aiding in the diagnosis of Alzheimer's disease according to claim 8, wherein the photoaffinity labeling reagent is activated by an ultraviolet light sufficient to effect photoactivation.

10. The method for aiding in the diagnosis of Alzheimer's disease according to claim 8, wherein the solubilized photoaffinity-labeled protein is separated by gel electrophoresis.

11. The method for aiding in the diagnosis of Alzheimer's disease according to claim 8, wherein the radioactively labeled photoaffinity labeling reagent is [$^{32}$P] 8-azidoadenosine-5'-triphosphate ([$^{32}$P]8N$_3$ATP) or [$^{32}$P]2-azidoadenosine-5'-triphosphate ([$^{32}$P]2N$_3$ATP).

12. The method for aiding in the diagnosis of Alzheimer's disease according to claim 8, in a patient afflicted with Alzheimer's disease, wherein the sample contains no detected [$^{32}$P]8N$_3$cAMP photolabeled protein at an apparent M$_r$ of about 68,000 daltons.

13. A method for aiding in the diagnosis of Alzheimer's disease in a mammal, comprising:
   a) contacting in the presence of micromolar levels of Mn$^{2+}$ ion a sample of cerebrospinal fluid which contains a nucleotide binding protein having an apparent M$_r$ of about 42,000 daltons wherein said protein is glutamine synthetase, with a labeled antibody specific for glutamine synthetase under conditions that allow the formation of glutamine synthetase-antibody complex formation;
   b) detecting the presence of said glutamine synthetase-antibody complexes; and
   c) correlating the presence of said complexes with the presence of Alzheimer's disease.

14. The method of claim 1, additionally comprising, before step (a), the step of removing small molecules from the proteins of a sample of CSF by dialysis or filtration.

15. The method of claim 14, wherein the glutamine synthetase-antibody complex formation is detected by enzyme linked immunosorbent assay, radioimmunoassay, immunoradiometric assay, sandwich immunoradiometric assay, fluoroimmunoassay, chemiluminescent assay, bioluminescent assay, or Western blot.

16. The method of claim 15, wherein the antibody specific for glutamine synthetase is labeled by binding to a second labeled antibody.

17. The method of claim 8, additionally comprising, before step (a), the step of removing small molecules from the proteins of a sample of CSF by dialysis or filtration.

18. The method of claim 1, wherein the Mn$^{2+}$ concentration is from 1.0 μM to 1000 μM.

19. The method of claim 1, wherein the Mn$^{2+}$ concentration is 10 μM.

20. The method of claim 8, wherein the Mn$^{2+}$ concentration is from 1.0 μM to 1000 μM.

21. The method of claim 8, wherein the Mn$^{2+}$ concentration is 10 μM.

* * * * *